(12) United States Patent
Deng et al.

(10) Patent No.: US 10,627,273 B2
(45) Date of Patent: Apr. 21, 2020

(54) ULTRASONIC FLOW RATE METERING

(71) Applicant: Sentec Ltd, Cambridge (GB)

(72) Inventors: Wenpeng Deng, Cambridge (GB); Jan Bennett, Cambridge (GB); David Healy, Stowmarket (GB); Andrew Nicholas Dames, Cambridge (GB); James William Evett, Winslow (GB)

(73) Assignee: Sentec Ltd., Cambridge (GB)

( * ) Notice: Subject to any disclaimer, the term of this patent is extended or adjusted under 35 U.S.C. 154(b) by 47 days.

(21) Appl. No.: 16/117,578

(22) Filed: Aug. 30, 2018

(65) Prior Publication Data

US 2019/0063970 A1 Feb. 28, 2019

(30) Foreign Application Priority Data

Aug. 30, 2017 (GB) .................................... 1713895.9

(51) Int. Cl.
*G01F 1/66* (2006.01)
*B06B 1/02* (2006.01)
(Continued)

(52) U.S. Cl.
CPC ............ *G01F 1/663* (2013.01); *B06B 1/0215* (2013.01); *G01F 1/662* (2013.01); *G01F 1/667* (2013.01);
(Continued)

(58) Field of Classification Search
CPC .............. G01F 1/66; G01F 15/06; B06B 1/02
See application file for complete search history.

(56) References Cited

U.S. PATENT DOCUMENTS 8,701,501 B2 * 4/2014 Miyata .................... G01F 1/667
73/861.18
9,551,603 B2 * 1/2017 Satou ...................... G01F 1/662
(Continued)

FOREIGN PATENT DOCUMENTS

EP 0145170 A1 6/1985
WO 199629575 A2 9/1996

OTHER PUBLICATIONS

Svilainis, L., et al., "Excitation Signal's Influence on Ultrasonic Transit Time Flow Meter's Performance," Kaunas University of Technology, Department of Signal Processing, all enclosed pages cited.
(Continued)

*Primary Examiner* — Jewel V Dowtin
(74) *Attorney, Agent, or Firm* — Burr & Forman LLP

(57) ABSTRACT

A method for an ultrasonic time-of-flight flow meter (1) includes driving an ultrasonic transducer (2, 3) using a first waveform ($V_1(t)$) for a first duration ($\Delta t_1$), the first waveform ($V_1(t)$) configured to cause oscillation (21) of the ultrasonic transducer (2, 3). The method also includes driving the ultrasonic transducer (2, 3) using a second waveform ($V_2(t)$) for a second duration ($\Delta t_2$). There is a discontinuity between the first waveform ($V_1(t)$) and the second waveform ($V_2(t)$). The second waveform ($V_2(t)$) and the second duration ($\Delta t_2$) are configured to maintain a voltage ($V_T(t)$) across the ultrasonic transducer (2, 3) within a predetermined range ($V_H$, $V_L$).

18 Claims, 14 Drawing Sheets

(51) Int. Cl.
*G01F 15/06* (2006.01)
*G01S 15/10* (2006.01)
*G01H 11/08* (2006.01)
*B06B 1/06* (2006.01)
*A61B 8/06* (2006.01)

(52) U.S. Cl.
CPC .......... *G01F 15/063* (2013.01); *G01F 15/066* (2013.01); *G01H 11/08* (2013.01); *G01S 15/104* (2013.01); *A61B 8/06* (2013.01); *B06B 1/0644* (2013.01)

(56) References Cited

U.S. PATENT DOCUMENTS

| | | | |
|---|---|---|---|
| 10,113,891 B2 * | 10/2018 | Nakai | B32B 5/26 |
| 10,422,674 B2 * | 9/2019 | Gestner | G01F 1/66 |
| 2003/0076742 A1 | 4/2003 | Rowe | |
| 2006/0005611 A1 | 1/2006 | Betz | |
| 2013/0080081 A1 | 3/2013 | Dugger et al. | |
| 2013/0239699 A1 * | 9/2013 | Ozaki | G01F 1/66 |
| | | | 73/861.28 |
| 2016/0284967 A1 | 9/2016 | Kruecken et al. | |

OTHER PUBLICATIONS

International Search Report and Written Opinion of PCT/GB2018/052447 dated Nov. 26, 2018, all enclosed pages cited.

* cited by examiner

ULTRASONIC FLOW RATE METERING

CROSS REFERENCE TO RELATED APPLICATION

This application claims priority to British application no. 1713895.9 filed Aug. 30, 2017, the entire contents of which are hereby incorporated by reference it its entirety.

FIELD OF THE INVENTION

The present invention relates to methods of ultrasonic flow rate metering using time-of-flight measurements, and flow rate meters employing the methods.

BACKGROUND

Ultrasonic flow rate meters have been constructed which measure a flow velocity of a liquid or gas based on time-of-flight measurements. Typically, a pair of ultrasonic transducers is arranged at opposite ends of a flow tube having a known length. Alternatively, a pair of ultrasonic transducers may be arranged spaced apart along the length of a flow tube by a distance, the ultrasonic transducers arranged at angles to the flow tube such that ultrasound may pass between the pair by reflecting from an internal wall or reflector of the flow tube. By obtaining time-of-flight measurements between the ultrasonic transducers both with, and against, the flow direction of the liquid or gas, a difference may be obtained which relates to the flow velocity of the liquid or gas.

For example, US 2013/080,081 A1 describes a fluid flow meter which estimates the velocity of water or another fluid flowing through a pipe by comparing measurements of the water velocity to one or more pre-determined templates. The fluid flow meter may collect measurement signals from one or more flow sensors (e.g., ultrasonic transducers), estimate the fluid velocity or flow rate by comparing the measurement signals to the template(s), and either store the comparison results in local memory, transmit the results to a remote memory or server, or both.

The use of variable frequency, or "chirp", excitation signals for ultrasonic transducers has been reported, see for example "Excitation signal's influence on ultrasonic transit time flow meter's performance", L Svilainis, P Kabisius, A Aleksandrovas and A Chaziachmetovas, TOP Conference Series, Materials Science and Engineering, Volume 42, conference 1, DOI: 10.1088/1757-899X/42/1/012047.

SUMMARY

According to a first aspect of the invention, there is provided a method for an ultrasonic time-of-flight flow meter. The method includes driving an ultrasonic transducer using a first waveform for a first duration, the first waveform configured to cause oscillation of the ultrasonic transducer. The method also includes driving the ultrasonic transducer using a second waveform for a second duration. There is a discontinuity between the first waveform and the second waveform. The second waveform and the second duration are configured to maintain a voltage across the ultrasonic transducer within a predetermined range.

The first waveform may include two or more distinct sub-waveforms, each sub-waveform of the first waveform configured to cause oscillation of the ultrasonic transducer. The second waveform may include two or more distinct sub-waveforms, each sub-waveform of the second waveform configured, in combination with the overall second duration, to maintain the voltage across the ultrasonic transducer within the predetermined range.

An ultrasonic time-of-flight flow meter may include first and second ultrasonic transducers spaced apart along a fluid flow path. The first and second ultrasonic transducers may be configured such that a transmission path between the first and second ultrasonic transducers has a component in a direction parallel to the fluid flow path.

The fluid flow path may be defined by a flow tube. The first and second ultrasonic transducers may be arranged at opposed ends of the flow tube. The first and second ultrasonic transducers may be oriented parallel to a flow direction oriented along the flow tube. The first and second ultrasonic transducers may be spaced apart along the length of the flow tube. The first and second ultrasonic transducers may be arranged at angles to the flow direction such that the transmission path between the first and second ultrasonic transducers includes at least one reflection from an internal wall of the flow tube. The first and second ultrasonic transducers may be arranged at angles to the flow direction such that the transmission path between the first and second ultrasonic transducers includes at least one reflection from a reflector element which is arranged within the flow tube, embedded in a wall of the flow tube, or integrally formed as part of a wall of the flow tube. The first and second ultrasonic transducers may be separated by a distance along the flow path.

The method may include alternating between driving the first ultrasonic transducer according to the method and receiving a signal using the second ultrasonic transducer, and driving the second ultrasonic transducer according to the method and receiving a signal using the first ultrasonic transducer. The first waveform may be configured to excite a recommended, or designed for, resonance of the driven ultrasonic transducer.

The discontinuity may be a discontinuity in one or more of frequency, gradient of frequency with respect to time, pulse width, duty-cycle and/or phase of the first and second waveforms. The discontinuity may take the form of a deviation between the last cycle or half-cycle of the first waveform and the first cycle or half cycle of the second waveform, the deviation being one or more of about 10% of frequency, about 10% of period, about 10% of pulse width, about 10% of duty cycle and/or more than about $\pi/8$ of phase.

The discontinuity may exist if the first waveform has a first fixed frequency and the second waveform has a second, different, fixed frequency. A discontinuity may exist if the first waveform is a first exponential chirp and the second waveform is a second, different, exponential chirp. A discontinuity may exist if the first waveform is a first linear chirp and the second waveform is a second, different, linear chirp. A discontinuity may exist if the first waveform is a first reciprocal chirp (1/x) and the second waveform is a second, different, reciprocal chirp. A discontinuity may exist if the first waveform is selected from a first group consisting of a first fixed frequency waveform, the first exponential chirp, the first linear chirp or the first reciprocal chirp, and if the second waveform is selected from a second group consisting of a second fixed frequency waveform, the second exponential chirp, the second linear chirp or the second reciprocal chirp.

A discontinuity factor, $D_f$ may be defined as $D_f=(f(t_1+\delta t)-f(t_1-\delta t))/f(t_1-\delta t)$, wherein f(t) is the frequency f at time t, $t_1$ is the time at the end of the first waveform, and $\delta t$ is a small increment of time, which may take values within the range 10 ns≤δt≤10 μs. The small increment of time δt may preferably be about 100 ns. Alternatively, the discontinuity factor may be defined as $D_f=(f(t_1+T(t_1))-f(t_1))/f(t_1)$, in which $f(t_1)$ is the end frequency of the first waveform and $T(t_1)=1/f(t_1)$ is the length of the final period of the first waveform. Whichever definition is used, a discontinuity may exist if the discontinuity factor is greater than or equal to 2. Whichever definition is used, a discontinuity may exist if the discontinuity factor is greater than or equal to 1. Whichever definition is used, a discontinuity may exist if the discontinuity factor is greater than or equal to 0.5.

The second duration may be configured to be sufficiently long to allow an oscillation energy of the ultrasonic transducer to reduce to a level whereby the voltage across the ultrasonic transducer will remain within the predetermined range after the end of the second duration.

The predetermined range may be a designed for driving voltage range of the ultrasonic transducer, or the designed for driving voltage range of the ultrasonic transducer plus an overvoltage tolerance. The predetermined range may be the designed for driving voltage of the ultrasonic transducer plus an overvoltage tolerance of ±5%, ±10% or ±15%.

The predetermined range may be a rail-to-rail voltage of a further component which is connected to the ultrasonic transducer in series or in parallel, or the rail-to-rail voltage of the further component plus an overvoltage tolerance. The predetermined range may be the rail-to-rail voltage of the further component plus an overvoltage tolerance of ±5%, ±10% or ±15%. The overvoltage tolerance of the further component may be ±1 mV, ±10 mV, ±200 mV or ±600 mV. The further component may be a switch, a multiplexer, an integrated circuit, and so forth. The method may prevent or reduce coupling between the ultrasonic transducer and one or more further ultrasonic transducers via intermediate components connecting the ultrasonic transducer to the one or more further ultrasonic transducers. For example, the method may prevent or reduce coupling between the first and second ultrasonic transducers. The predetermined range may be between and including −0.2 V to 3.5 V. The predetermined range may be between and including −0.2 V to 5.2 V.

The first waveform may have a frequency spectrum in which a majority of the power is within one or more bandwidths corresponding to respective resonances of the ultrasonic transducer, and the second waveform may have a frequency spectrum in which a majority of the power is outside the one or more bandwidths corresponding to respective resonances of the ultrasonic transducer.

The first waveform may have a frequency spectrum in which 50% or more, 60% or more, 70% or more, 80% or more, or 90% or more of the power is within the one or more bandwidths corresponding to respective resonances of the ultrasonic transducer. The second waveform may have a frequency spectrum in which 50% or more, 60% or more, 70% or more, 80% or more, or 90% or more of the power is outside the one or more bandwidths corresponding to respective resonances of the ultrasonic transducer.

The first waveform may have a substantially constant base frequency. The second waveform may have a substantially constant base frequency. Depending upon the application, the term "substantially" may correspond to a tolerance of ±5%, or ±10%.

The frequency of the first waveform may vary as a function of time. The frequency of the first waveform may vary linearly as a function of time. The frequency of the first waveform may vary exponentially as a function of time. The frequency of the first waveform may vary reciprocally as a function of time. The first waveform may take the form of a chirp.

The frequency of the second waveform may vary as a function of time. The frequency of the second waveform may vary linearly as a function of time. The frequency of the second waveform may vary exponentially as a function of time. The frequency of the second waveform may vary reciprocally as a function of time. The second waveform may take the form of a chirp.

The second waveform may have a phase shift of between and including π/2 to 3π/2 with respect to the first waveform, and the second duration may be insufficient to cause oscillation of the ultrasonic transducer in response to the second waveform.

The second duration may be insufficient to generate significant oscillation of the ultrasonic transducer. The second duration may be configured such that a maximum amplitude of any voltage oscillation induced across the ultrasonic transducer following the end of the second waveform is less than or equal to 200 mV. The ultrasonic transducer may be a piezoelectric transducer.

The method may be used to measure the flow rate of a liquid. The method may be used to measure the flow rate of a gas. The method may be used to measure the flow rate of water. The method may be used to measure the flow rate of natural gas. The method may be used to measure a flow rate used for fiscal metering purposes.

According to a second aspect of the invention, there is provided an ultrasonic time-of-flight flow meter, including a first ultrasonic transducer and a second ultrasonic transducer spaced apart along a fluid flow path and configured such that a transmission path between the first and second ultrasonic transducers has a component in a direction parallel to the fluid flow path. The ultrasonic time-of-flight flow meter also includes a controller configured to drive the first and second ultrasonic transducers alternately. The controller is configured to drive the driven ultrasonic transducer using a first waveform for a first duration. The first waveform is configured to cause oscillation of the driven ultrasonic transducer. The controller is also configured to drive the driven ultrasonic transducer using a second waveform for a second duration. There is a discontinuity between the first waveform and the second waveform. The second waveform and the second duration are configured to maintain a voltage across the driven ultrasonic transducer within a predetermined range.

The fluid flow path may be defined by a flow tube. The first and second ultrasonic transducers may be arranged at opposed ends of a flow tube. The first and second ultrasonic transducers may be oriented parallel to a flow direction oriented along the flow tube. The first and second ultrasonic transducers may be spaced apart along the length of the flow tube. The first and second ultrasonic transducers may be arranged at angles to the flow direction such that the transmission path between the first and second ultrasonic transducers includes at least one reflection from an internal wall of the flow tube. The first and second ultrasonic transducers may be arranged at angles to the flow direction such that the transmission path between the first and second ultrasonic transducers includes at least one reflection from a reflector element which is arranged within the flow tube, embedded in a wall of the flow tube, or integrally formed as part of a wall of the flow tube.

The first waveform may be configured to excite a recommended, or designed for, resonance of the first and/or second ultrasonic transducer.

The discontinuity may be a discontinuity in one or more of the senses defined with reference to the method.

The second duration may be configured to be sufficiently long to allow an oscillation energy of the driven ultrasonic transducer to reduce to a level whereby the voltage across the driven ultrasonic transducer will remain within the predetermined range after the end of the second duration.

The predetermined range may be defined in the same way as for the method.

The first waveform may have a frequency spectrum in which a majority of the power is within one or more bandwidths corresponding to respective resonances of the driven ultrasonic transducer, and the second waveform may have a frequency spectrum in which a majority of the power is outside the one or more bandwidths corresponding to respective resonances of the driven ultrasonic transducer.

The first waveform may have a frequency spectrum in which 50% or more, 60% or more, 70% or more, 80% or more, or 90% or more of the power is within the one or more bandwidths corresponding to respective resonances of the driven ultrasonic transducer. The second waveform may have a frequency spectrum in which 50% or more, 60% or more, 70% or more, 80% or more, or 90% or more of the power is outside the one or more bandwidths corresponding to respective resonances of the driven ultrasonic transducer.

The first waveform may have a substantially constant base frequency. The second waveform may have a substantially constant base frequency. Depending upon the application, the term "substantially" may correspond to a tolerance of ±5%, or ±10%.

The frequency of the first waveform may vary as a function of time. The frequency of the first waveform may vary linearly as a function of time. The frequency of the first waveform may vary exponentially as a function of time. The frequency of the first waveform may vary reciprocally as a function of time. The first waveform may take the form of a chirp.

The frequency of the second waveform may vary as a function of time. The frequency of the second waveform may vary linearly as a function of time. The frequency of the second waveform may vary exponentially as a function of time. The frequency of the second waveform may vary reciprocally as a function of time. The second waveform may take the form of a chirp.

The second waveform may have a phase shift of between and including $\pi/2$ to $3\pi/2$ with respect to the first waveform, and the second duration may be insufficient to cause significant oscillation of the driven ultrasonic transducer in response to the second waveform. The second duration may be configured such that a maximum amplitude of any voltage oscillation induced across the driven ultrasonic transducer following the end of the second waveform is less than or equal to 200 mV. The ultrasonic transducer may be a piezoelectric transducer.

The second waveform may be configured to suppress coupling between the first and second ultrasonic transducers.

A base frequency of the second waveform may be greater than 1.1 times a primary resonant frequency of the ultrasonic transducer. A base frequency of the second waveform may be greater than 2 times the primary resonant frequency of the driven ultrasonic transducer. A base frequency of the second waveform may be greater than 3 times the primary resonant frequency of the ultrasonic transducer. A base frequency of the second waveform may be greater than 10 times the primary resonant frequency of the ultrasonic transducer.

A base frequency of the second waveform may be less than 0.9 times a primary resonant frequency of the ultrasonic transducer. A base frequency of the second waveform may be less than 0.5 times the primary resonant frequency of the ultrasonic transducer. A base frequency of the second waveform may be less than 0.2 times the primary resonant frequency of the ultrasonic transducer. A base frequency of the second waveform may be less than 0.1 times the primary resonant frequency of the ultrasonic transducer. A base frequency of the second waveform may be less than 0.01 times the primary resonant frequency of the ultrasonic transducer.

The ultrasonic transducer may be a piezoelectric transducer. The ultrasonic transducer may be a solenoid transducer.

A distance separating the first and second ultrasonic transducers along the fluid flow path may be less than 25 mm, less than 50 mm, less than 70 mm, less than 100 mm, less than 200 mm or less than 500 mm.

BRIEF DESCRIPTION OF THE DRAWINGS

Certain embodiments of the present invention will now be described, by way of example, with reference to the accompanying drawings in which.

DETAILED DESCRIPTION OF CERTAIN EMBODIMENTS

Figure 1:
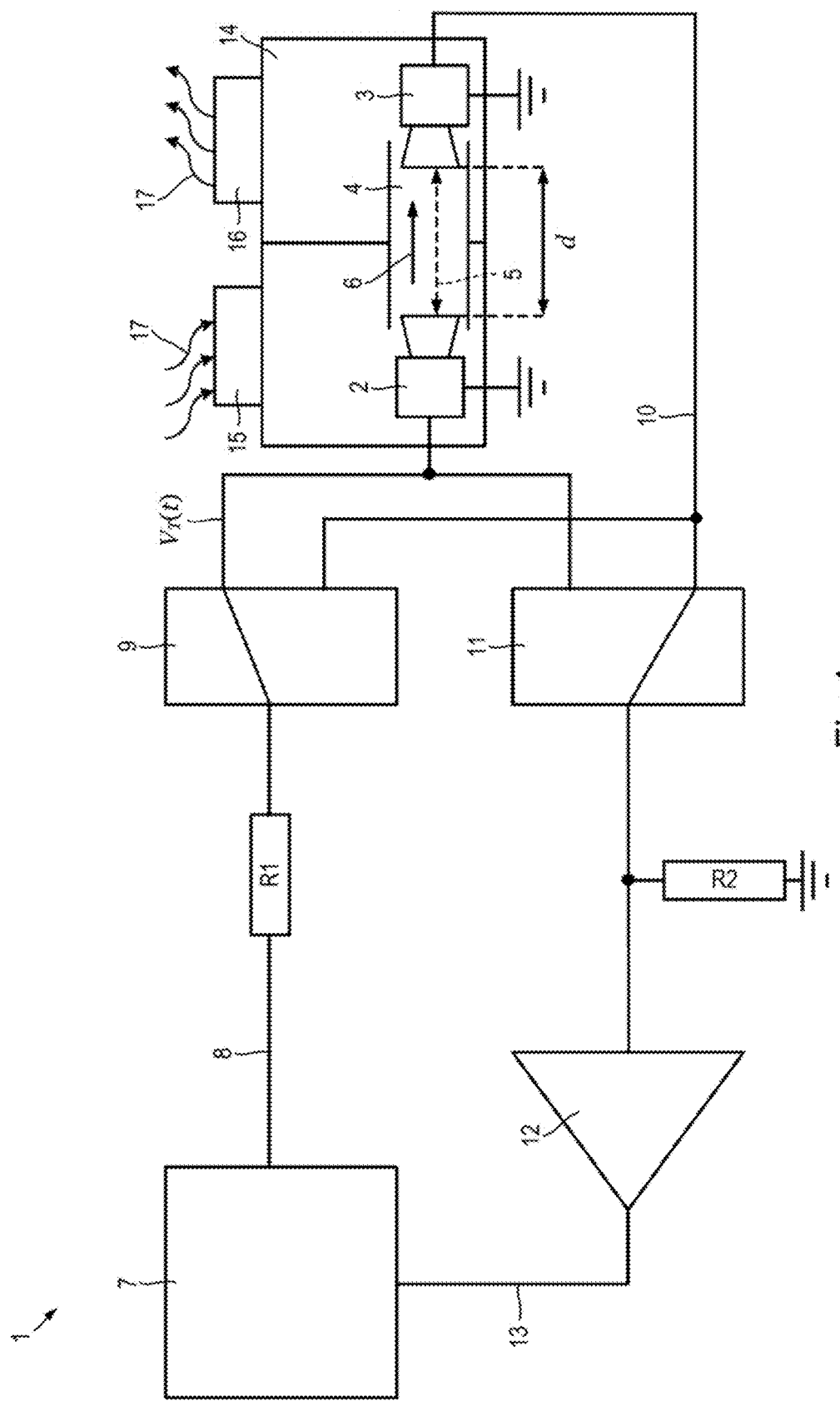
FIG. 1 illustrates an ultrasonic time-of-flight flow rate meter.

In the following, like parts are denoted by like reference numbers.

The specification relates to the use of ultrasonic transducers. Once an ultrasonic transducer has begun oscillating, the ultrasonic transducer stores an oscillation energy which is associated with the motion. This oscillation energy will dissipate with time without continuous energy input. However, when an excitation signal to an ultrasonic transducer is stopped, the oscillation energy causes the ultrasonic transducer to continue oscillating, giving rise to an effect termed "ringing". This ringing, if not properly managed, can cause various problems for ultrasonic time-of-flight based flow measurements.

According to previous methods for operating ultrasonic transducers, at the end of a transmit pulse, a transmit driver is set to, for example, either 0 V or a +ve rail voltage. The resonant oscillation of the ultrasonic transducer continues following the end of the transmit pulse. This oscillation may induce a ringing voltage across the ultrasonic transducer, which is now clamped to, for example, either 0 V or the +ve rail voltage. In other examples, differential driving may be used. Using differential driving may mean that neither side of the ultrasonic transducer is clamped to ground or 0 V. The induced ringing voltage may drive other components to which the ultrasonic transducer is connected, for example a multiplexer or an active semiconductor component, beyond the power rail voltage and/or overvoltage tolerance. This may reverse bias such connected components. If an overvoltage tolerance is exceeded, leakage currents may flow from the transmitting ultrasound transducer to other parts of the circuit. In some cases, the leaked current originating from the ringing voltage may be coupled into a receiver amplifier and/or a receiving ultrasound transducer. Such coupling may cause interference with flow rate measurements.

A non-exhaustive list of some of the problems which may result from ringing voltages induced in transmitting ultrasonic transducers includes:

Unwanted coupling to connected electronics;
Interference with measurements;
Causing cycle slips (this refers to one or more cycles being missed by the receiver, leading to an error of the corresponding number of periods);
Timing errors in "time of flight" measurements; and
Increasing the minimum required separation distance of transmit and receive ultrasonic transducers.

Several approaches for mitigating the effects of induced ringing voltages in transmitting ultrasound transducers have been considered. For example, a clamping diode may be fitted to an ultrasonic transducer, or connected components, to prevent excessive over-voltages.

Alternatively, additional discrete components may be added in the form of a clamping circuit connected to the ultrasonic transducer, for example a MOSFET controlled circuit configured to become conductive and drain energy from a transmitting ultrasonic transducer once the transmit pulse is finished.

Other options include using a digital to analogue converter (DAC) plus buffer and/or filter to drive a transmitting ultrasonic transducer, or using line drives that can drive middle rail voltages.

The problem with these previous approaches is that the number of components and the complexity for an ultrasonic flow meter are increased, with consequences for the size, cost and long term reliability of the flow meter. These approaches may also add capacitance, make matching the ultrasonic transducers more difficult, decrease the coupled energy, and/or decrease efficiency. A consequence of the additional non-matching components is that the zero flow offset of the flow rate meter may be increased.

Finally, it is also possible to simply accept the problem of induced ringing voltages, and to increase the separation between paired ultrasonic transducers in an attempt to ensure that ringing voltages in the transmitting ultrasonic transducer have decayed before the transmitted pulse reaches the receiving ultrasonic transducer.

This approach is also unsatisfactory because the size of a flow rate meter must be increased to accommodate a larger distance between paired ultrasonic transducers. Increasing the distance also has the effect of increasing the energy needed to make measurements. In general, the greater the distance, the more acoustic attenuation will occur before a transmitted pulse reaches a receiving ultrasonic transducer. In order to maintain a given signal-to-noise ratio over a greater distance, more energy is needed in the drive pulse, for example, a higher drive voltage or an increase in the number of pulses. Flow meters may often be used for long term installations in locations where there is no mains electric connection available, and may need to operate using battery power or energy harvesting, so that the energy required for measurements is a consideration.

The present specification is concerned with methods to manage induced ringing voltages of transmitting ultrasonic transducers. The methods of the present specification do not require additional electronic components, and may be implemented within simple, compact and cheap ultrasonic flow rate meters. Consequently, the methods of the present specification may allow a relatively low zero-flow offset to be maintained.

Referring to FIG. 1, an ultrasonic time-of-flight flow rate meter 1 is shown.

The ultrasonic time-of-flight flow rate meter 1 includes a first ultrasonic transducer 2 and a second ultrasonic transducer 3. The first and second ultrasonic transducers 2, 3 are spaced apart along a fluid flow path 6 in the form of a flow tube 4. The first and second transducers 2, 3 are configured such that a transmission path 5 between the first and second ultrasonic transducers 2, 3 has a component in a direction parallel to the fluid flow path 6. In the example shown in FIG. 1, the first and second ultrasonic transducers 2, 3 are arranged at opposite ends of the flow tube 4. The ultrasonic transducers 2, 3 are separated by a distance, d, in the direction parallel to the fluid flow path 6. The ultrasonic transducers 2, 3 may be piezoelectric transducers, solenoid transducers, and so forth.

The ultrasonic time-of-flight flow rate meter 1 also includes a controller 7, which is configured to drive the first and second ultrasonic transducers 2, 3 alternately. The controller 7 may be a microcontroller, a microprocessor, or any other suitable data processing apparatus. In order to make a measurement of flow rate, the controller 7 may drive the first ultrasonic transducer 2 and measure a first time-of-flight Δt/based on reception of the signal at the second ultrasonic transducer 3. The controller 7 then measures a second time of flight $\Delta t_2$ by driving the second ultrasonic transducer 3 and receiving the signal at the first ultrasonic transducer 2. If the fluid in the fluid flow tube 4, which may be a gas or a liquid, is moving away from the first ultrasonic transducer 2 and towards the second ultrasonic transducer 3 with a velocity, v, along the fluid flow path 6 then the first and second times-of-flight may be expressed as:

$$t_{f1} = \frac{d}{v+c} \quad (1)$$

$$t_{f2} = \frac{d}{c-v}$$

In which $t_{f1}$ is the time-of-flight from the first ultrasonic transducer 2 to the second ultrasonic transducer 3, $t_{f2}$ is the time-of-flight from the second ultrasonic transducer 3 to the first ultrasonic transducer 2, d is the spacing of the ultrasonic transducers 2, 3, v is the fluid velocity and c is the speed of sound in the fluid 17. The equations may be re-arranged to provide an expression for the velocity of the fluid:

$$v = d \frac{t_{f2} - t_{f1}}{2 t_{f1} t_{f2}} \quad (2)$$

The controller 7 is configured to drive the respective ultrasonic transducer 2, 3, i.e. the first or second ultrasonic transducer 2, 3 currently acting as transmitter, using a first waveform $V_1/(t)$ for a first duration $\Delta t = t_1 - t_0$, in which to is the time at which excitation of the transmitting ultrasonic transducer 2, 3 is started and $t_1$ is the time at the end of the first waveform $V_1(t)$. The first waveform $V_1(t)$ is configured to cause oscillation of the transmitting ultrasonic transducer 2, 3. The first waveform $V_1(t)$ may be configured to excite a recommended, or designed for, resonance of the first and/or second ultrasonic transducer 2, 3. For example, if an ultrasonic transducer 2, 3 has a recommended resonance centred at a primary resonance frequency $f_1$, then the first waveform $V_1(t)$ preferably includes all, or a majority of, the signal power at frequencies lying within a bandwidth $\delta f_1$ centred around the primary resonance frequency $f_1$.

Following the first duration $\Delta t_1$, the controller 7 is configured to drive the transmitting ultrasonic transducer 2, 3 using a second waveform $V_2(t)$ for a second duration $\Delta t_2 = t_2 - t_1$, in which $t_2$ is the time at the end of the second waveform $V_2(t)$. The second waveform $V_2(t)$ and the second duration $\Delta t_2$, are configured to maintain a voltage $V_T$ across the transmitting ultrasonic transducer 2, 3 within a predetermined range $V_H$, $V_T$. For example, the second waveform $V_2(t)$ may include frequencies outside the bandwidth $\delta f_1$ centred around the primary resonance frequency $f_1$, or preferably outside the bandwidths corresponding to any resonances of the ultrasonic transducers 2, 3. Alternatively, the second waveform $V_2(t)$ may be in full or partial anti-phase with the first waveform $V_1(t)$, so as to oppose and dampen the oscillations of the transmitting ultrasonic transducer 2, 3. In this latter case, the second duration $\Delta t_2$ should be sufficiently short to avoid re-exciting the transmitting ultrasonic transducer 2, 3 after the initial damping of oscillatory motion.

The controller 7 drives the ultrasonic transducer 2, 3 using pulsed or square waveforms having variable frequency, duty cycle and so forth. The controller 7 may output either a high rail voltage, $V_{RH}$, or a low rail voltage $V_{RL}$, and the first and second waveforms $V_1(t)$, $V_2(t)$ alternate between high voltage $V_{RH}$ and low voltage $V_{RL}$. This configuration allows the flow rate meter 1 to be simple and compact, with low mismatch of components, permitting relatively low zero-flow offset.

According to the methods of the present specification, there should be a discontinuity between the first waveform $V_1(t)$ and the second waveform $V_2(t)$. The discontinuity may take many forms, for example, the discontinuity may be in the frequencies of the first and second waveforms $V_1(t)$, $V_2(t)$. For example, the first waveform $V_1(t)$ may have a fixed base frequency $f_{B1}$ and the second waveform $V_2(t)$ may have a different fixed base frequency $f_{B2} \neq f_{B1}$. The first and second waveforms $V_1(t)$, $V_2(t)$ need not have fixed base frequencies, and in some examples one or both of the base frequencies $f_{B1}$, $f_{B2}$ may be functions of time, i.e. $f_{B1}(t)$, $f_{B2}(t)$. In such examples, the discontinuity may occur in the values of base frequency, i.e. $f_{B1}(t_1) \neq f_{B2}(t_1)$. Waveforms in which the base frequency changes over time are sometimes referred to as "chirps". Typical types of chirp include a linear chirp having a frequency varying according to:

$$f_B(t) = \alpha t + \beta \quad (3)$$

In which $f_B(t)$ is the base frequency of either the first waveform $f_{B1}(t)$ or the second waveform $f_{B2}(t)$, α is a gradient and β is a constant. Another type of chirp is an exponential chirp having a frequency varying according to:

$$f_B(t) = \gamma e^{\varepsilon t} \quad (4)$$

In which γ and ε are constants. A further type of chirp is a reciprocal chirp having a frequency varying according to:

$$f_B(t) = \frac{\rho}{t + \tau} \quad (5)$$

In which ρ is a scaling constant and τ is an optional constant included to avert divergence for t→0.

The first waveform $V_1(t)$ may be any one of a fixed frequency signal, a linear chirp, an exponential chirp, a reciprocal chirp, and so forth. Independently of the first waveform $V_1(t)$, the second waveform $V_2(t)$ may be any one of a fixed frequency signal, a linear chirp, an exponential chirp, a reciprocal chirp, and so forth.

Additionally or alternatively, the discontinuity may occur in the gradients of base frequency $f_{B1}(t)$, $f_{B2}(t)$ with respect to time:

$$\left. \frac{df_{B1}}{dt} \right|_{t_1} \neq \left. \frac{df_{B2}}{dt} \right|_{t_1} \quad (6)$$

Other forms which the discontinuity may take include a discontinuity in phase between the first and second waveforms $V_1(t)$, $V_2(t)$. For example:

$$V_1(t) = V_0 e^{-i f B t + \varphi 1}$$

$$V_2(t) = V_0 e^{-i f B t + \varphi 2} \quad (7)$$

In which $V_0$ is an amplitude and in which the phase $\varphi_1 \neq \varphi_2$.

In some examples according to the present specification, the discontinuity may take the form of a deviation between the last cycle or half-cycle of the first waveform $V_1(t)$ and the first cycle or half cycle of the second waveform $V_2(t)$, the deviation being one or more of 10% of frequency, 10% of period, 10% of pulse width, 10% of duty cycle and/or more than $\pi/8$ of phase.

In practical circumstances, it may be useful to define a discontinuity factor, $D_f$, as $D_f = (f_{B2}(t_1+\delta t) - f_{B1}(t_1-\delta t))/f_{B1}(t_1-\delta t)$, in which $\delta t$ is a small increment of time, which may take values within the range $10 \text{ ns} \leq \delta t \leq 10 \text{ }\mu\text{s}$. The small increment of time $\delta t$ may preferably be about 100 ns. Alternatively, the discontinuity factor may be defined as $D_f = (f(t_1+T(t_1)) - f(t_1))/f(t_1)$, in which $f(t_1)$ is the end frequency of the first waveform $V_1(t)$ and $T(t_1)=1/f(t_1)$ is the length of the final period of the first waveform $V_1(t)$. Whichever definition is used, in some examples the discontinuity factor $D_f$ is preferably greater than or equal to 2. In other examples the discontinuity factor $D_f$ may be greater than or equal to 1. In further examples the discontinuity factor $D_f$ may be greater than or equal to 0.5.

For example, if the base frequency $f_{B1}$ of the first waveform $V_1(t)$ is 440 kHz just before the end $t_1$ of the first duration $\Delta t_1$, then in an example of the method using a discontinuity factor of $D_f=3.55$, the base frequency $f_{B2}$ of the second waveform $V_2(t)$ would be 2 MHz just after the start of the second duration $\Delta t_2$. Alternatively, if the method was implemented using a discontinuity factor of $D_f=1$, then the base frequency $f_{B2}$ of the second waveform $V_2(t)$ would be 880 kHz just after the start of the second duration $\Delta t_2$. In a further example, if the method was implemented using a discontinuity factor of $D_f=0.5$, then the base frequency $f_{B2}$ of the second waveform $V_2(t)$ would be 660 kHz just after the start of the second duration $\Delta t_2$.

Further examples of the first waveform $V_1(t)$, the second waveform $V_2(t)$ and the discontinuity are described hereinafter. The hereinbefore described types of discontinuity are not mutually exclusive. In examples according to the present specification, multiple types of the hereinbefore described discontinuities may exist simultaneously between the first waveform $V_1(t)$ and the second waveform $V_2(t)$.

The second duration $\Delta t_2$ is preferably configured to be sufficiently long to allow an energy associated with the oscillation of the first or second ultrasonic transducer 2, 3 to reduce to a level whereby the voltage $V_T$ across the first or second ultrasonic transducer 2, 3 will remain within the predetermined range $V_H$, $V_T$ after the end of the second duration $\Delta t_2$. An appropriate second duration $\Delta t_2$ may be determined from calibration experiments, by varying the second duration $\Delta t_2$ and measuring the amplitude of any induced ringing voltage which occurs at the end of the second duration $\Delta t_2$. Individual calibration of each ultrasonic time-of-flight flow rate meter 1 is not necessary. Provided that calibration experiments are performed using a sampling of ultrasonic time-of-flight flow rate meters 1 which is large enough to capture the variance in performance, a single value of the second duration $\Delta t_2$ may be determined for use with subsequently constructed ultrasonic time-of-flight flow rate meters 1.

The key components of an ultrasonic time-of-flight flow rate meter 1 for implementing methods of the present specification are the first and second ultrasonic transducers 2, 3, the flow tube 4 and the controller 7, as described hereinbefore. For context FIG. 1 shows further components of one example of an ultrasonic time-of-flight flow rate meter 1.

The controller 7 outputs a drive signal 8 to the transmitting ultrasonic transducer 2, 3 via a first impedance matching resistor R1 and a first switch or multiplexer 9. The first switch 9 may be controlled to supply the drive signal 8 to either the first ultrasonic transducer 2 or the second ultrasonic transducer 3. Whichever ultrasonic transducer 2, 3 receives the drive signal 8 is the transmitting ultrasonic transducer for a measurement. The drive signal 8 includes or consists of the hereinbefore described first and second waveforms $V_1(t)$, $V_2(t)$. The first impedance matching resistor R1 may have a value of 820Ω.

Whichever ultrasonic transducer 2, 3 does not receive the drive signal 8 is the receiving ultrasonic transducer for a measurement. The receiving ultrasonic transducer 2, 3 detects an ultrasound signal from the transmitting ultrasonic transducer 2, 3, and converts it into a received electrical signal 10. The received signal 10 is returned to the controller 7 via a second switch or multiplexer 11 and a signal conditioning circuit 12. The first and second switches 9, 11 are configured so that when, for example, the first switch 9 connects to the first ultrasonic transducer 2, the second switch 11 will connect to the second ultrasonic transducer 3, and vice-versa. The signal conditioning circuit 12 may perform amplification and or filtering of the received signal 10 to generate a conditioned signal 13. The controller 7 determines a time-of-flight by comparing the drive signal 8 with the conditioned signal 13. A second matching resistor R2 may have a value of 820Ω.

The flow tube 4 is contained within an enclosure 14 having a fluid inlet 15 and a fluid outlet 16. The enclosure 14 is arranged so that fluid 17 entering the fluid inlet 15 can only pass to the fluid outlet 16 by passing along the fluid flow path 6 through the flow tube 4. The fluid 17 may be a liquid or a gas. For example, the fluid 17 may be water or natural gas.

The methods of the present specification will be principally explained with reference to the ultrasonic time-of-flight flow rate meter 1 shown in FIG. 1. However, as noted hereinbefore, the methods of the present specification are not limited to this configuration of an ultrasonic time-of-flight flow rate meter 1.

Alternative Time-of-Flight Measurement Configurations

Figure 2:
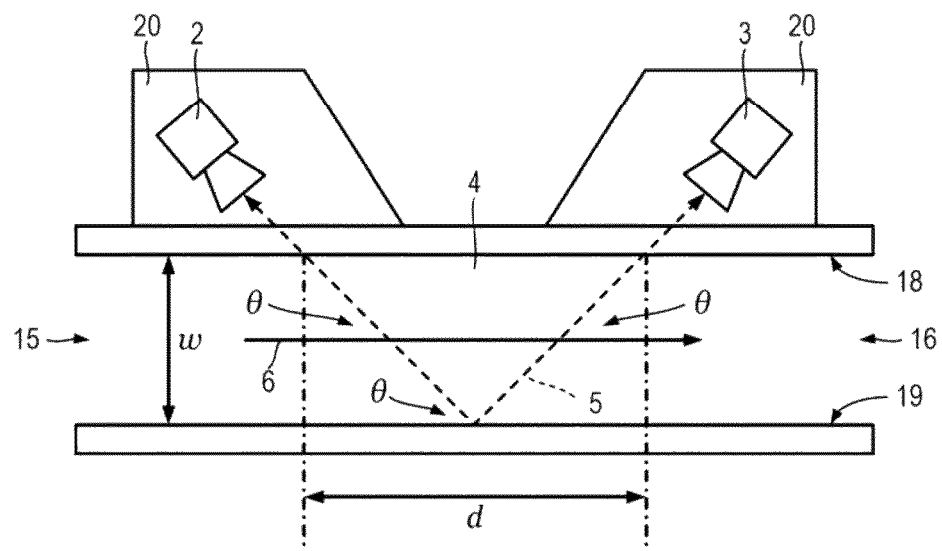
FIG. 2 illustrates an alternative configuration for ultrasonic time-of-flight flow rate measurements.

Referring also to FIG. 2, a first alternative configuration for time-of-flight measurements using first and second ultrasonic transducers 2, 3 is shown.

Instead of being arranged at opposed ends of the flow tube 4, the first and second ultrasonic transducers 2, 3 may be offset from the fluid flow path 6 formed by the flow tube 4, and oriented at angles ±θ to the fluid flow path 6. Both ultrasonic transducers 2, 3 are arranged on a first side 18 of the flow tube 4. The transmission path 5 includes a reflection from a second side 19 of the flow tube 4, opposed to the first side 18. The flow tube 4 may include a separate reflector (not shown), or the second side 19 of the flow tube 4 may be integrally formed to function as a suitable reflector for the transmission path 5. The component of the length of the transmission path 5 that is within the flow tube 4 and parallel to the fluid flow path 6 has length d, such that if the width of the flow tube 4 is w, then $\tan(\theta)=2w/d$. Provided that the geometry is known or may be calibrated, Equations (1) and (2) may be adapted for time-of-flight based flow rate measurements using the configuration shown in FIG. 2. In practice, a flow-rate meter may be calibrated using at least one flow rate of fluid passing through the meter, which compensates for various parameters including the physical geometry of the meter.

The first and second ultrasonic transducers 2, 3 may be external to the flow tube 4, as shown in FIG. 2. In such a configuration, first and second ultrasonic transducers 2, 3 may be connected to the flow tube 4 using impedance matching materials 20 to enhance transmission of ultrasound in and/or out of the flow tube 4. Alternatively, the first and/or second ultrasonic transducers 2, 3 may be embedded within, or integrally formed as part of, a wall providing the first side 18.

Figure 3:
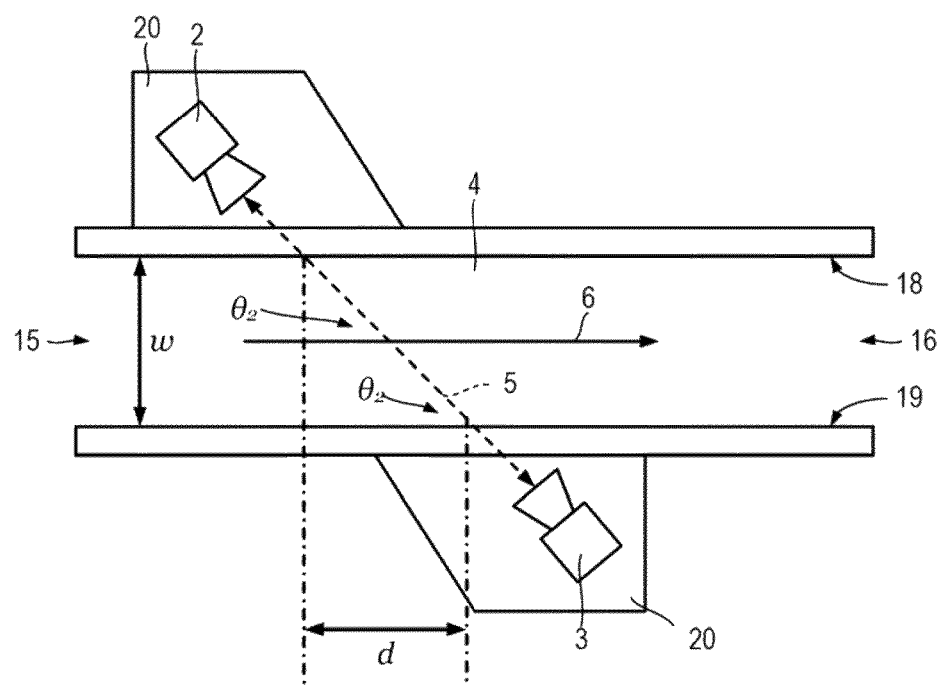
FIG. 3 illustrates an alternative configuration for ultrasonic time-of-flight flow rate measurements.

Referring also to FIG. 3, a second alternative configuration for time-of-flight measurements using first and second ultrasonic transducers 2, 3 is shown.

The second alternative configuration of first and second ultrasonic transducers 2, 3 is similar to the first alternative configuration shown in FIG. 2, except that the second ultrasonic transducer 3 is arranged on the second side 19 of the flow tube 4, such that the transmission path 5 does not include a reflection, and such that $\tan(\theta_2)=w/d$.

Ringing in an Ultrasonic Time-of-Flight Flow Rate Meter

Figure 4:
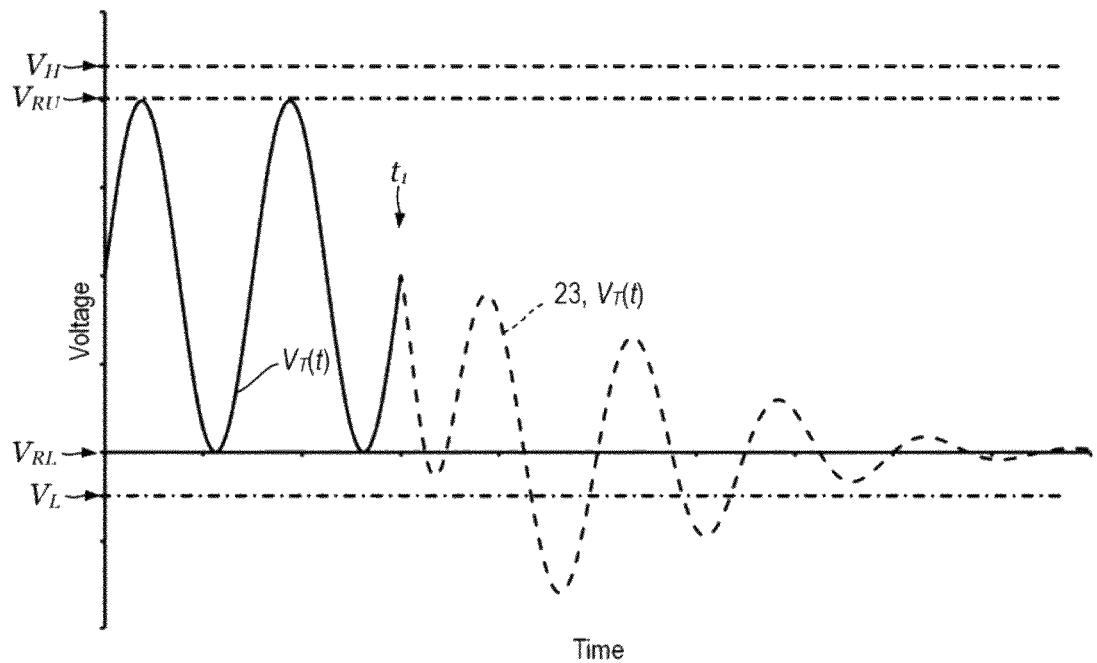
FIG. 4 illustrates ringing of an ultrasonic transducer after the end of a driving signal.
Figure 5:
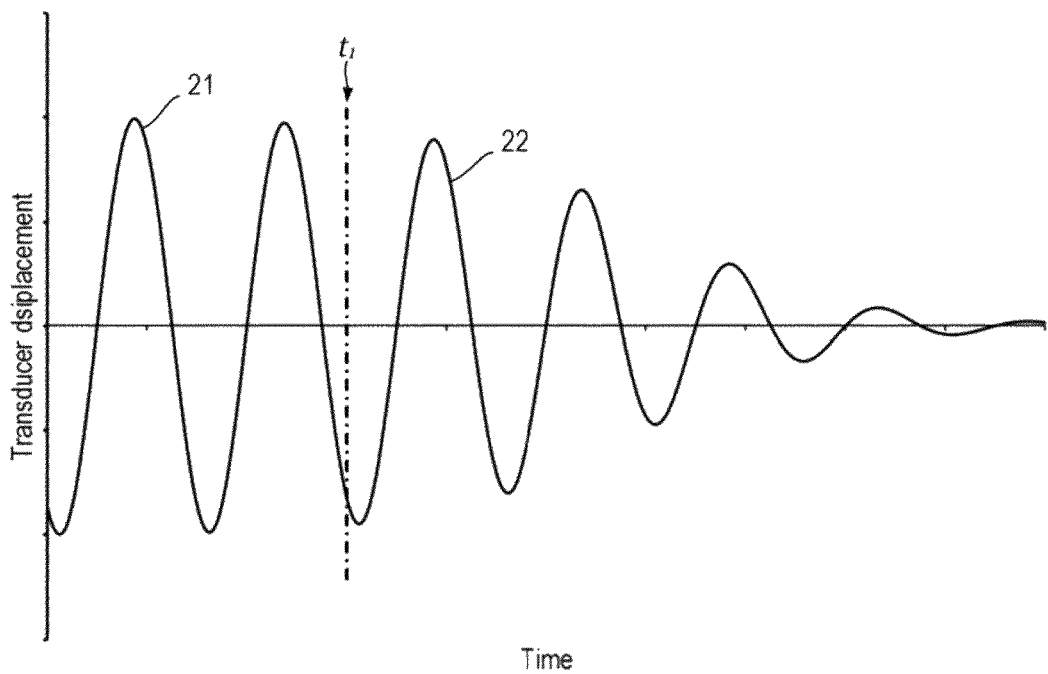
FIG. 5 illustrates self-oscillation of an ultrasonic transducer after the end of a driving signal.

Referring also to FIGS. 4 and 5, the induced ringing voltages which the presently described methods may reduce or prevent will be further explained. In the example shown in relation to FIGS. 4 and 5, the drive signal 8 only includes the first waveform $V_1(t)$.

Referring in particular to FIG. 4, the voltage $V_T(t)$ across the transmitting ultrasonic transducer 2, 3 is illustrated. It should be noted that the voltage $V_T(t)$ across the transmitting ultrasonic transducer 2, 3 may not be identical to the drive signal 8 as a result of the finite capacitance and inductance of the circuit. In particular, the first waveform $V_1(t)$ of the drive signal 8 in the illustrated example takes the form of a square or pulsed waveform which varies between an upper rail voltage $V_{RU}$ and a lower rail voltage $V_{RL}$.

When the drive signal 8 supplied to a transmitting ultrasonic transducer finishes, the ideal situation would be that the ultrasonic transducer 2, 3 stops vibrating immediately. For example, ideally the oscillation 21 of the ultrasonic transducer 2, 3 should stop when the first waveform $V_1(t)$ ends at time $t_1$.

However, in reality the ultrasonic transducers 2, 3 will not stop immediately because of the remaining oscillation energy, and the ultrasonic transducer will undergo a self-oscillation 22 which decays over time. As a consequence of the nature of the ultrasonic transducer 2, 3 as a device for converting between voltage and displacement, the self-oscillation 22 of the ultrasonic transducer 2, 3 will induce a ringing voltage 23, across the ultrasonic transducer 2, 3. When the output which supplies the drive signal 8 is clamped to, for example, $V_{RL}=0$ V at the end of the first waveform $V_1(t)$, the superposition of the induced ringing voltage 23 may cause the voltage across the ultrasonic transducer $V_T(t)$ to drop below the lower bound $V_L$ of the predetermined range, for example the lower rail voltage $V_{RL}$ plus an overvoltage tolerance. Similar behaviour may occur with respect to the upper bound $V_H$ of the predetermined range, for example the upper rail voltage $V_{RU}$ plus an overvoltage tolerance, if the output which supplies the drive signal 8 is clamped to the upper rail voltage $V_{RU}$ at the end of the first waveform $V_1(t)$. In the example shown in FIG. 4, the bounds $V_H$, $V_L$ of the predetermined range are respectively slightly above and below the upper and lower rail voltages $V_{RU}$, $V_{RL}$, reflecting an over-voltage tolerance of the circuitry before significant current leakage occurs. Depending on the application, an over-voltage tolerance may correspond to, for example, ±5%, ±10% or ±15% of the range $V_{RU}V_{RL}$ between the upper and lower rail voltages $V_{RU}$, $V_{RL}$. Depending on the application, an over-voltage may correspond to, for example below −0.2 V and above 3.5 V.

The induced ringing voltage 23 may be detrimental to the operation of an ultrasonic time-of-flight flow rate meter 1. For example, the induced ringing voltage 23 may cause interference to connected or coupled electronics if the voltage $V_T(t)$ across the ultrasonic transducer 2, 3 exceeds the predetermined range $V_H$, $V_L$. For example, if the first ultrasonic transducer 2 is driven and the subsequent induced ringing voltage 23 exceeds the predetermined range $V_H$, $V_L$, then the induced ringing voltage may couple to the second ultrasonic transducer 3. Such coupling may be misinterpreted as a received signal 10. For example, such coupling may occur as a result of current leakage to the conditioning circuit 12 via the second switch 11, in response to the induced ringing voltage 23 exceeding an overvoltage tolerance of the second switch 11.

Such interference may be detrimental because it makes the effective drive signal 8 longer and prohibits the use of short and/or compact flow tubes 4, because there needs to be some "quiet" time to separate the transmitted and received pulses to avoid coupled interference due to the induced ringing voltage from overlapping in time with the real received signal 10. Furthermore, the induced ringing voltage 23 and associated interference injected to other parts of the ultrasonic time-of-flight flow rate meter 1 may distort a correlation or timing algorithm executed by the controller 7. The hereinbefore described problems are not an exhaustive description of the problems which may be caused by induced ringing voltages 23 in an ultrasonic time-of-flight flow rate meter 1. The problem of induced ringing voltages 23 may arise in measurements of any fluid, including natural gas and water.

In general, the predetermined range $V_H$, $V_L$ may be a designed for driving voltage range of the first or second ultrasonic transducers 2, 3. The predetermined range $V_H$, $V_L$ may extend beyond the designed for driving voltage range of the first or second ultrasonic transducers 2, 3 by an over-voltage tolerance margin. Alternatively, the predetermined range $V_H$, $V_L$ may be a designed for rail-to-rail voltage $V_{RU}$, $V_{RL}$, of a further component which is connected to the first or second ultrasonic transducers 2, 3. For example, the predetermined range $V_H$, $V_L$ may be a designed for rail-to-rail voltage $V_{RU}$, $V_{RL}$, of first and/or second switches 9, 11. The predetermined range $V_H$, $V_L$ may extend beyond the designed for rail-to-rail voltage $V_{RU}$, $V_{RL}$, of a further component which is connected to the first or second ultrasonic transducers 2, 3 by an overvoltage tolerance margin. For example, in a circuit designed to use a 3.3 V supply, the predetermined range may be between and including −0.2 V to 3.5 V. In a further example of a circuit designed to use a 5 V supply, the predetermined range may be between and including −0.2 V to 5.2 V.

By maintaining the voltage $V_T(t)$ across an ultrasonic transducer 2, 3 within a predetermined range $V_H$, $V_L$, the methods of the present specification may prevent or reduce coupling between a transmitting ultrasonic transducer 2, 3 and one or more receiving ultrasonic transducers 2, 3. For example, the methods of the present specification may prevent or reduce coupling between the first ultrasonic transducer 2 and the second ultrasonic transducer 3 via the first and/or second switches 9, 11, and vice versa.

Figure 6:
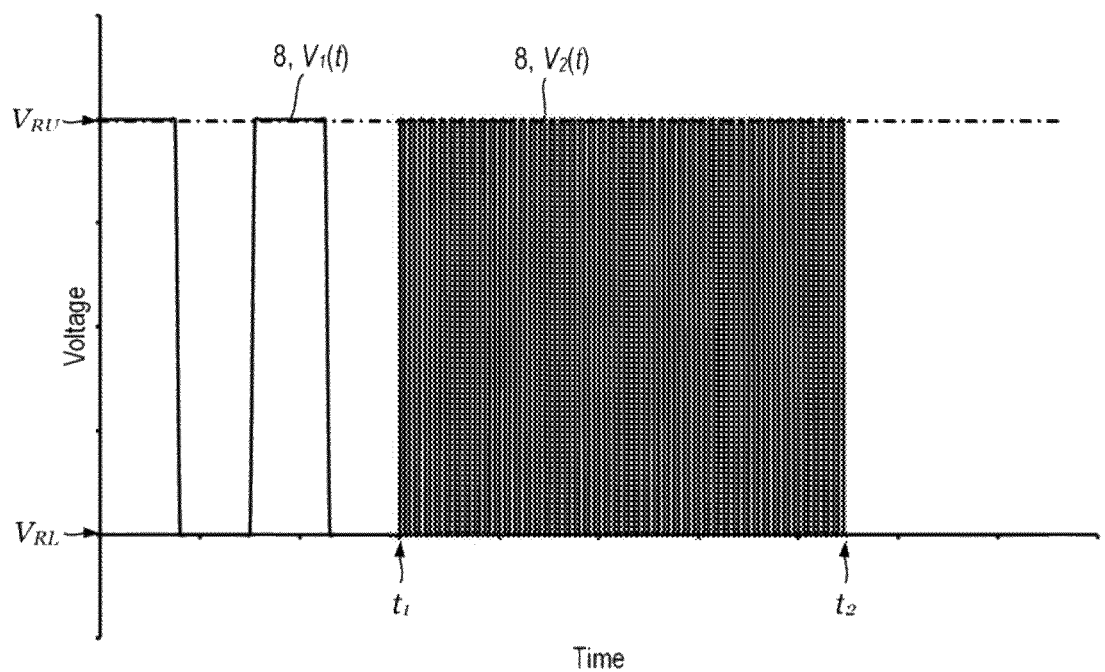
FIG. 6 illustrates an example of a driving signal including first and second waveforms.
Figure 7:
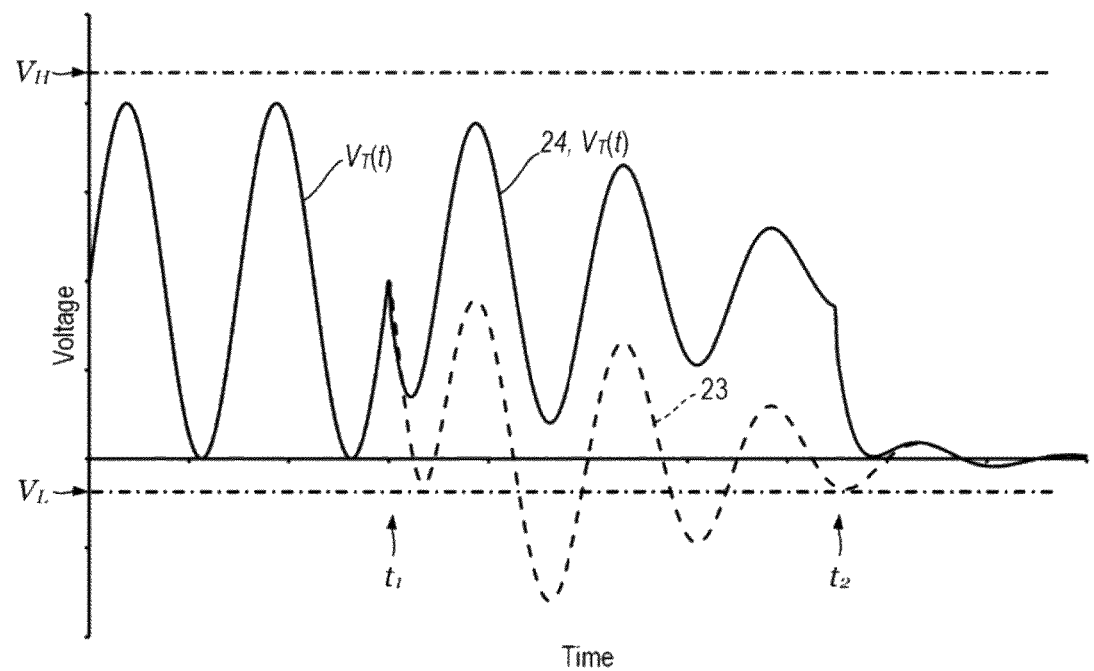
FIG. 7 illustrates modified ringing of an ultrasonic transducer after the end of a driving signal.

First Method of Maintaining a Voltage Across an Ultrasonic Transducer within a Predetermined Range Referring also to FIGS. 6 and 7, a first example of the method is illustrated.

The transmitting ultrasonic transducer 2, 3 is driven using a drive signal 8 which includes a first waveform $V_1(t)$ followed by a second waveform $V_2(t)$. The first and second waveforms $V_1(t)$, $V_2(t)$ are both square or pulsed waveforms between a lower rail voltage $V_{RL}$ and an upper rail voltage $V_{RU}$. The first waveform $V_1(t)$ is used to drive the transmitting ultrasonic transducer 2, 3 for the first duration $\Delta t_1$ between time to (not shown in FIGS. 6 and 7) and time $t_1$. During the first period $\Delta t_1$, the first waveform $V_1(t)$ excites oscillation 21 of the ultrasonic transducer 2, 3. The first waveform $V_1(t)$ has a base frequency $f_{B1}$ which is within the bandwidth $\delta f_1$ of a primary resonance frequency $f_1$ of the ultrasonic transducer 2, 3.

After time $t_1$, the drive signal 8 switches to the second waveform $V_2(t)$ for the second duration $\Delta t_2$ for $t_1 < t \leq t_2$. The second waveform $V_2(t)$ and the second duration $\Delta t_2$ are configured to maintain the voltage $V_T(t)$ across the ultrasonic transducer 2, 3 within the predetermined range $V_H$, $V_L$. The second waveform $V_2(t)$ has a base frequency $f_{B2}$ which is outside the bandwidth $\delta f_1$ of a primary resonance frequency $f_1$ of the ultrasonic transducer 2, 3 (or any other resonances $f_2$, $f_3$ of the ultrasonic transducer 2, 3). Thus, in this example the discontinuity is a discontinuity in the base frequencies $f_{B1}$, $f_{B2}$. Consequently, the second waveform $V_2(t)$ does not excite further oscillation 21 of the ultrasonic transducer 2, 3. The self-oscillation 22 of the ultrasonic transducer 2, 3 is not significantly modified by the second waveform $V_2(t)$, i.e. the self-oscillation 22 is not damped. However, the rapid cycling of the second waveform $V_2(t)$ maintains an average voltage output from the controller 7 close to the centre of the predetermined range $V_H$, $V_L$. As a result, a modified ringing voltage 24 resulting from the self-oscillation 22 of the ultrasonic transducer 2, 3 is relatively more centred within the predetermined range $V_H$, $V_L$, about the average value of the second waveform $V_2(t)$, thereby reducing the probability of the voltage $V_1(t)$ across the ultrasonic transducer 2, 3 exceeding the predetermined range $V_H$, $V_L$.

The second duration $\Delta t_2$ is preferably configured to be sufficiently long to allow the self-oscillation 22 of the ultrasonic transducer 2, 3 to reduce to a level whereby the voltage $V_T(t)$ across the ultrasonic transducer 2, 3 will remain within the predetermined range $V_H$, $V_L$ after the end of the second duration $\Delta t_2$. For example, as shown in FIG. 7, when the second waveform $V_2(t)$ ends at time $t_2$, the amplitude of the self-oscillation 22 has reduced sufficiently that the residual ringing is small enough to that it does not drop below the lower bound $V_L$ of the predetermined range.

In summary, the first example of the method concerns appending a discontinuous, out-of-band second waveform $V_2(t)$ at the end of the first waveform $V_1(t)$. Because the second waveform $V_2(t)$ has a base frequency $f_{B2}$ outside of the bandwidth $\delta f_1$ of the primary resonance $f_1$ (or any other resonances $f_2$, $f_3$), the ultrasonic transducer 2, 3 effectively filters the second waveform $V_2(t)$ by itself. The second waveform $V_2(t)$ also has the effect of holding the ultrasonic transducer 2, 3 in, or at least closer to, the middle of its operating range, thereby allowing the self-oscillation 22 to decay in a controlled manner and avoiding the ringing voltage 23 behaviour observed when only the first waveform $V_1(t)$ is used.

Figure 8:
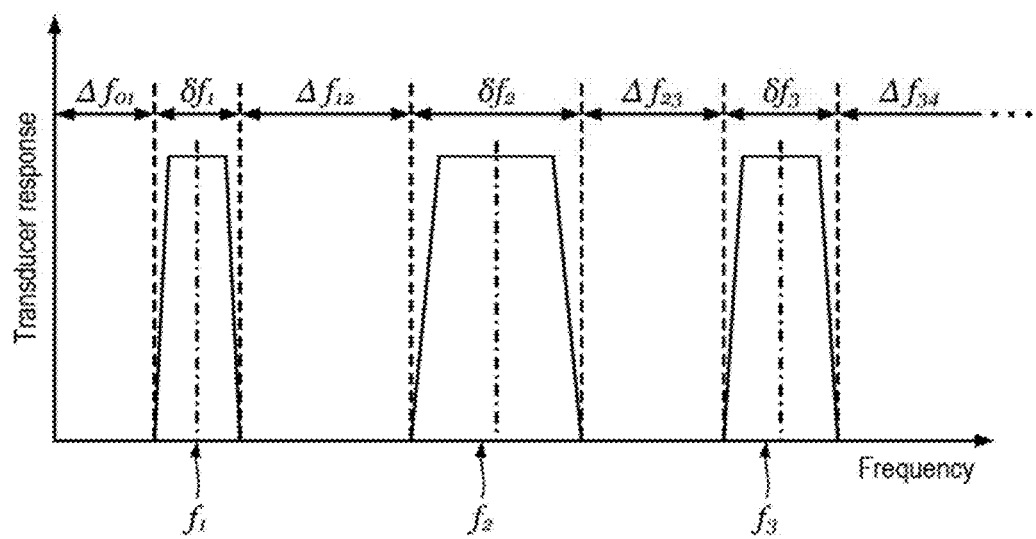
FIG. 8 is a schematic illustration of a frequency response of an ultrasonic transducer.

Referring also to FIG. 8, a schematic frequency response of an ultrasonic transducer 2, 3 is shown.

In addition to a primary resonance frequency $f_1$ having an associated bandwidth $\delta f_1$, an ultrasonic transducer may include further resonance frequencies $f_2$, $f_3$ and so forth, each of which is associated with a corresponding bandwidth $\delta f_2$, $\delta f_3$ and so forth. Although three resonances $f_1$, $f_2$, $f_3$ are shown in FIG. 8, there is no upper limit on the number of resonances frequencies $f_1$, $f_2$, $f_3$. Between the resonant bandwidths $\delta f_1$, $\delta f_2$, $\delta f_3$, there are inert bandwidths $\Delta f_{01}$, $\Delta f_{12}$, $\Delta f_{23}$, $\Delta f_{34}$, and so forth. Frequencies within the inert bandwidths $\Delta f_{01}$, $\Delta f_{12}$, $\Delta f_{23}$, $\Delta f_{34}$ cause very little, or no, response in the ultrasonic transducer 2, 3.

In some examples the higher resonant frequencies $f_2$, $f_3$ and so forth may represent harmonics of the primary resonance frequency $f_1$. However, in general the behaviour of the ultrasonic transducer 2, 3 may be more complex, and the higher resonant frequencies $f_2$, $f_3$ need not be harmonics of the primary resonance frequency $f_1$.

According to the first example of the method, the first waveform $V_1(t)$ should have a frequency spectrum in which a majority of the signal power is within one or more bandwidths $\delta f_1$, $\delta f_2$, $\delta f_3$ corresponding to respective resonances $f_1$, $f_2$, $f_3$ of the ultrasonic transducer 2, 3. Additionally, the second waveform $V_2(t)$ should have a frequency spectrum in which a majority of the signal power is outside the one or more bandwidths $\delta f_1$, $\delta f_2$, $\delta f_3$ corresponding to respective resonances $f_1$, $f_2$, $f_3$ of the ultrasonic transducer. In other words, the second waveform $V_2(t)$ should have a frequency spectrum in which a majority of the signal power is within one or more inert bandwidths $\Delta f_{01}$, $\Delta f_{12}$, $\Delta f_{23}$, $\Delta f_{34}$ of the ultrasonic transducer 2, 3.

For example, the first waveform $V_1(t)$ may have a frequency spectrum in which 50% or more, 60% or more, 70% or more, 80% or more, or 90% or more of the power is within the one or more bandwidths $\delta f_1$, $\delta f_2$, $\delta f_3$ corresponding to respective resonances $f_1$, $f_2$, $f_3$ of the ultrasonic transducer 2, 3. The second waveform $V_2(t)$ may have a frequency spectrum in which 50% or more, 60% or more, 70% or more, 80% or more, or 90% or more of the power is outside the one or more bandwidths $\delta f_1$, $\delta f_2$, $\delta f_3$ corresponding to respective resonances $f_1$, $f_2$, $f_3$ of the ultrasonic transducer 2, 3.

Figure 9:
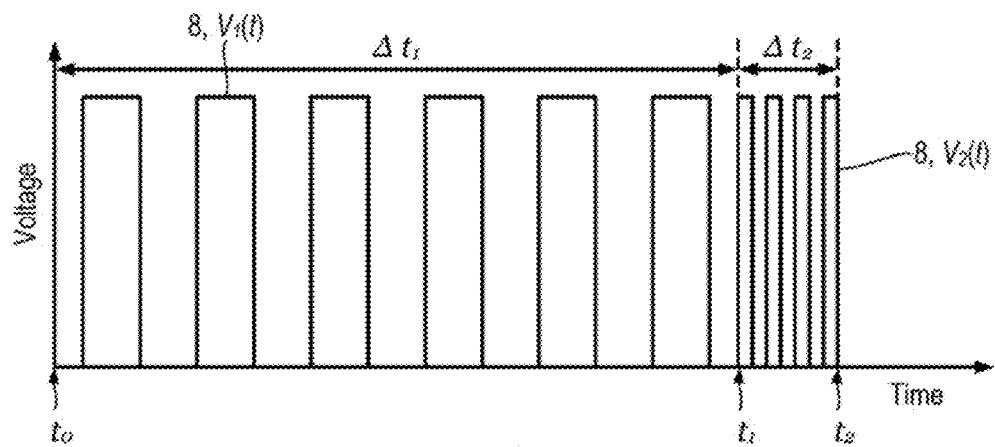
FIG. 9 illustrates an example of a driving signal including first and second waveforms.

Referring also to FIG. 9, a complete drive signal 8 including the first and second waveforms $V_1(t)$, $V_2(t)$ is illustrated.

The first waveform $V_1(t)$ includes a number of pulses having a base frequency $f_{B1}$ within the bandwidth $\delta f_1$ of a primary resonance $f_1$ of an ultrasonic transducer 2, 3. After the end of the first duration $\Delta t_1$, the second waveform $V_2(t)$ is also a pulsed waveform. However, the base frequency $f_{B2}$ of the second waveform $V_2(t)$ is outside the bandwidth $\delta f_1$ of a primary resonance $f_1$ of an ultrasonic transducer 2, 3. In the example shown, $f_{B2}$ is within the inert bandwidth $\Delta f_{12}$ between the primary resonance frequency $f_1$ and a secondary resonance frequency $f_2$.

Second Method of Maintaining a Voltage Across an Ultrasonic Transducer within a Predetermined Range A second example of the method is similar to the first example, except that the form of the discontinuity between the first and second waveforms $V_1(t)$, $V_2(t)$ is different.

Figure 10:
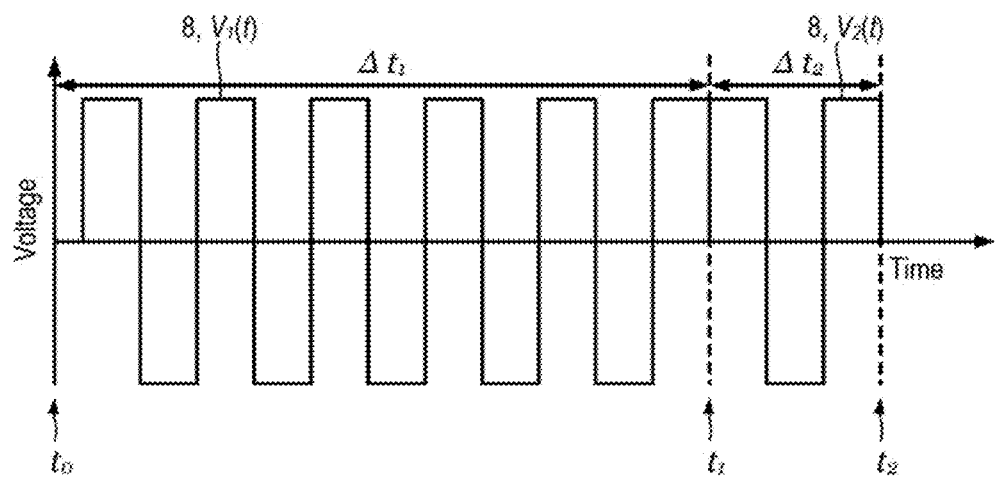
FIG. 10 illustrates an example of a driving signal including first and second waveforms.

Referring also to FIG. 10, schematic waveforms $V_1(t)$, $V_2(t)$ according to the second example are shown.

Unlike the first example, the second waveform $V_2(t)$ is configured to apply frequencies within the bandwidth $\delta f_1$ of the primary resonance $f_1$, or the bandwidths $\delta f_3$, $\delta f_2$ of further resonant frequencies $f_2$, $f_3$. In some examples, the frequencies of the first and second waveforms may be continuous, i.e. $f_{B1}(t_1)$ $f_{B2}(t_2)$. Instead, in the second example of the method, the phase is discontinuous between the first and second waveforms $V_1(t)$, $V_2(t)$.

For example, the second waveform $V_2(t)$ shown in FIG. 10 has the same constant base frequency $f_{B2}$ as the first waveform $V_1(t)$, i.e. $f_{B2}=f_{B1}$. However, the second waveform $V_2(t)$ has a phase shift of 7C with respect to the first waveform $V_1(t)$. Consequently, the second waveform $V_2(t)$ will actively dampen the self-oscillation 22 of the ultrasonic transducer 2, 3. If the second duration $\Delta t_2$ goes on for long enough, the second waveform $V_2(t)$ would start to drive oscillations 21 of the ultrasonic transducer 2 in the opposite sense to the first waveform $V_1(t)$. However, the length of the second duration $\Delta t_2$ is configured to be just sufficient to dampen, or arrest, the self-oscillation 22 of the ultrasonic transducer 2, and not significantly longer.

An appropriate length of the second duration $\Delta t_2$ may be determined from calibration experiments using a number of representative ultrasonic transducers 2, 3. Provided that the sampling of ultrasonic transducers 2, 3 used for such calibration experiments captures the typical variance between ultrasonic transducers 2, 3, there will be no need to calibrate each ultrasonic transducer 2, 3 individually.

Although a phase discontinuity of 7C will be most effective, any phase discontinuity in the range between and including $\pi/2$ to $3\pi/2$ may be used in the second method.

Measurements of Coupling between Transmission and Reception Channels

Figure 11:
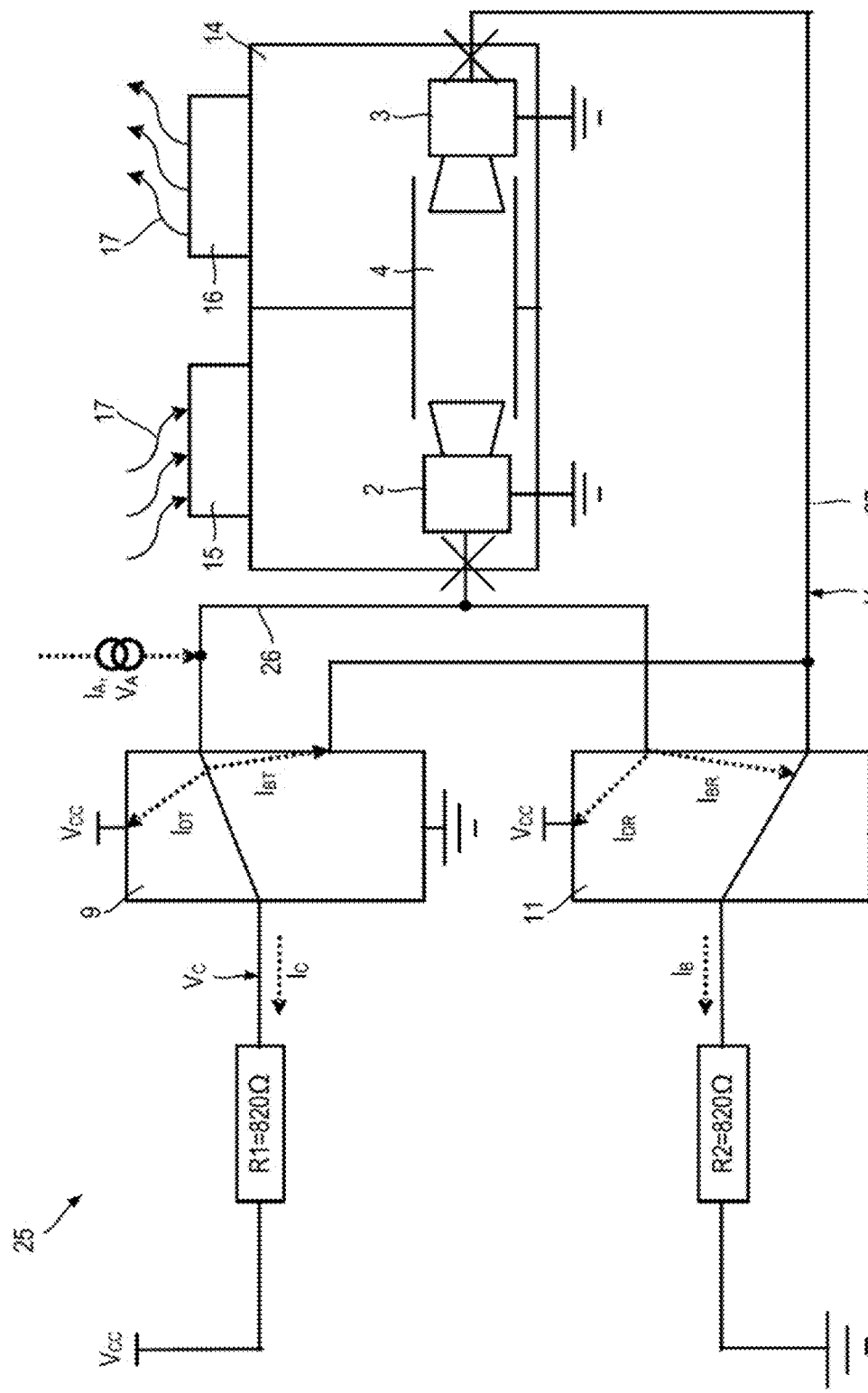
FIG. 11 illustrates an arrangement for measuring leakage current between transmitting and receiving pathways of an ultrasonic time-of-flight flow rate meter.

Referring also to FIG. 11, an arrangement 25 for measuring the extent of coupling between transmission and reception channels of an ultrasonic time-of-flight flow rate meter 1 is shown.

The arrangement 25 is similar to the ultrasonic time-of-flight flow rate meter 1, except that the ultrasonic transducers 2, 3 are disconnected and the controller 7 and signal conditioning circuit 12 are omitted. A voltage $V_A$ was applied to a first node 26 which connects the outputs of the first and second switches 9, 11 which would normally be connected to the first ultrasonic transducer 2. A total current $I_A$ injected to the first node 26 was measured. The input to the first switch 9 was connected to the supply voltage $V_{RU}=V_{CC}=3.3V$ via a first impedance matching resistor $R1=820\Omega$. The input to the second switch 11 was connected to ground (GND) via a second matching resistor $R2=820\Omega$. The voltage $V_A$ was greater than $V_{CC}$ in these experiments.

At the same time, a voltage VB was also measured on a second node 27 which connects the ports of the first and second switches 9, 11 which would normally be connected to the second ultrasonic transducer 3. A current $I_B$ from the second node 27 to ground via the second matching resistor R2 was calculated. In an ideal case, and when $V_A$ remains within the supply rail voltages, $V_{RL}=$GND to $V_{RU}=V_{CC}$, or alternatively when $V_A$ remains within a predetermined range $V_H$, $V_L$, the voltage $V_B$ on the second node 27 and the current $I_B$ to ground via the second matching resistor R2 should be zero.

When $V_A$ is outside the supply rail voltages $V_{RU}=V_{CC}$, $V_{RL}=$GND, the switches 9, 11 may become reverse biased or electrostatic discharge (ESD) protection may be triggered. This may cause current coupling between the first and second nodes 26, 27 through the first and/or second switches 9, 11, so that $I_B$ and $V_B$ are no longer zero.

Figure 12:
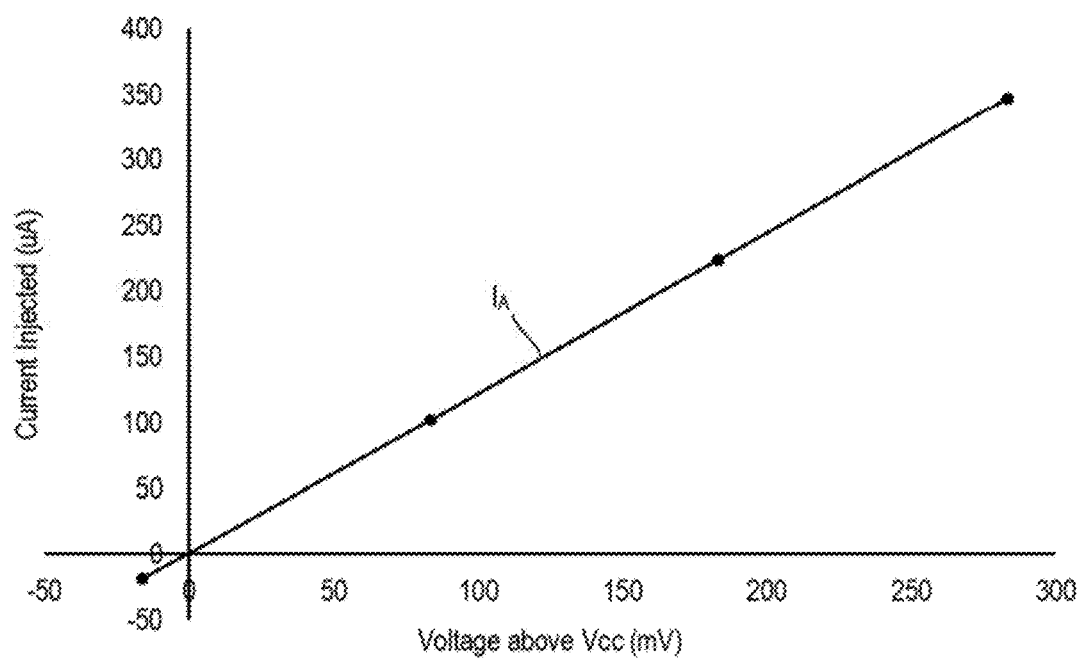
FIG. 12 presents measurements of a current injected to the arrangement of FIG. 11 as a function of applied voltage.

Referring also to FIG. 12, the injected current $I_A$ is plotted as a function of the voltage $V_A$ applied to the first node 29.

Figure 13:
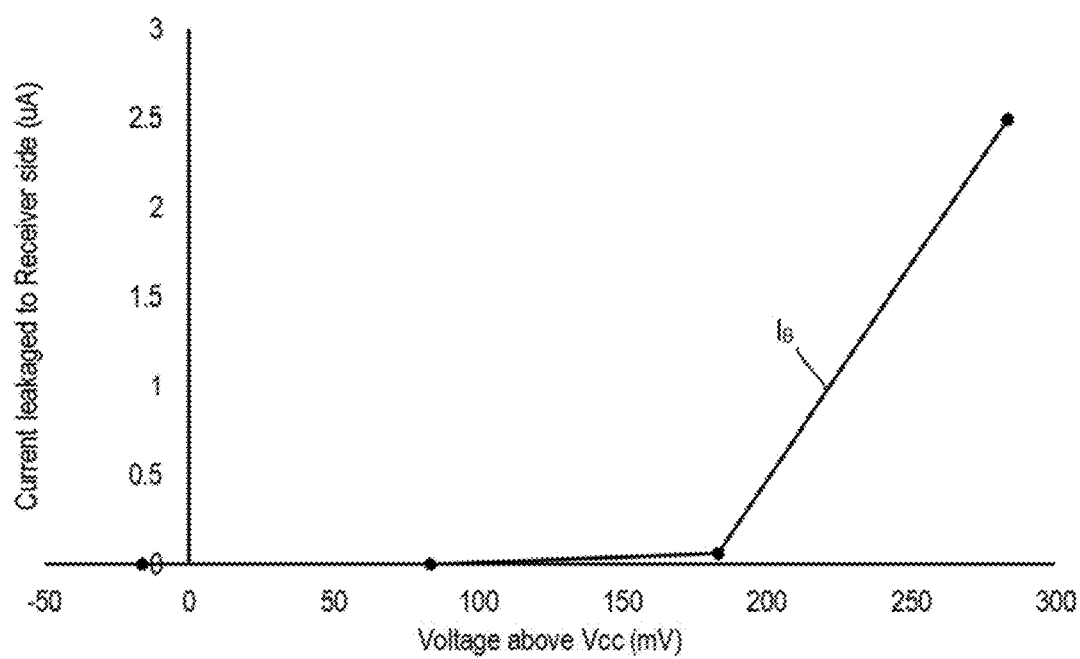
FIG. 13 presents measurements of a leakage current in the arrangement of FIG. 11 as a function of applied voltage.

Referring also to FIG. 13, the leakage current $I_B$ is plotted as a function of the voltage $V_A$ applied to the first node 26.

It may be observed from FIG. 13 that as the voltage $V_A$ applied to the first node 26 increases to above around 200 mV greater than the rail voltage $V_{RC}=V_{cc}$, the leakage current $I_B$ begins to increase significantly. This suggests an overvoltage tolerance of approximately 200 mV. When the first and second ultrasonic transducers 2, 3 are attached, overvoltages caused by induced ringing voltages 23 may also leak to the received signal 10 path in a similar way.

Experimental Observations of Ringing

Figure 14:
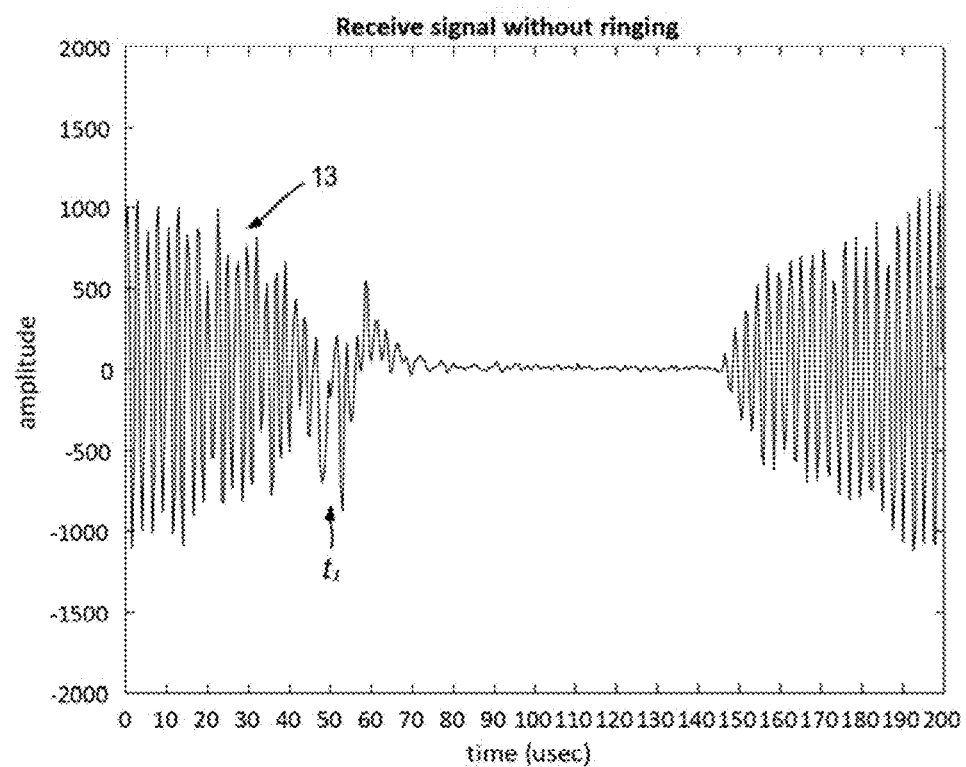
FIG. 14 presents measurements of a received signal which is not affected by ringing.
Figure 15:
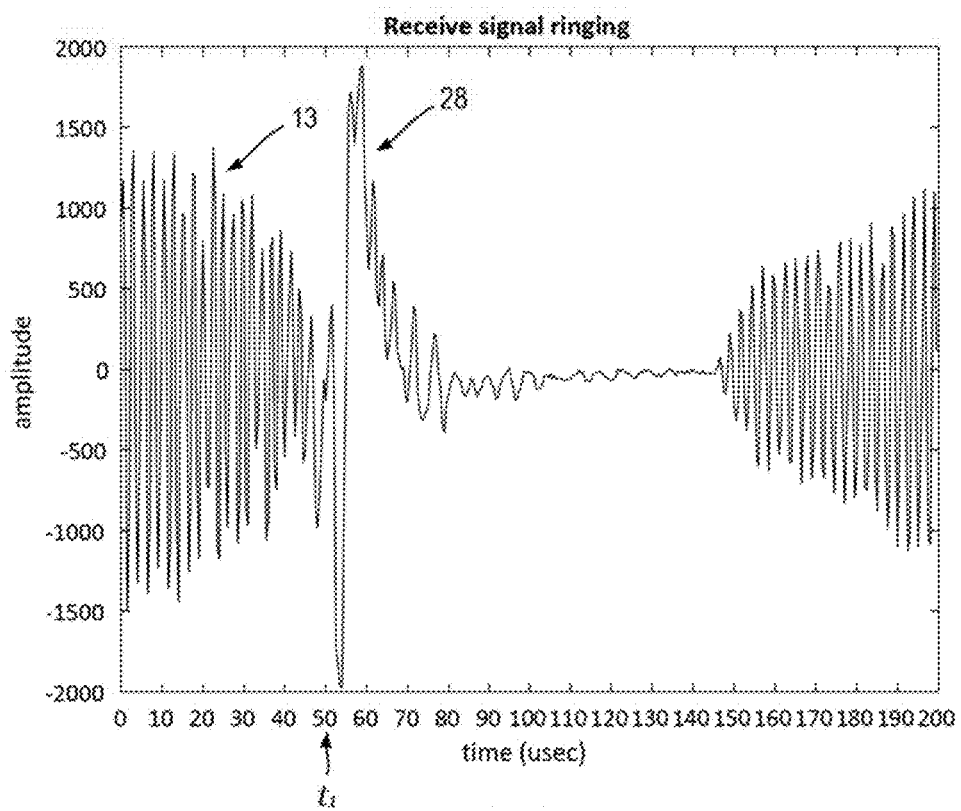
FIG. 15 presents measurements of a received signal which is affected by ringing.

Referring also to FIGS. 14 and 15, measurements of interference caused by ringing voltages 23 are presented.

FIG. 14 presents a measurement of the received signal 10 when the self-oscillation 22 of the transmitting ultrasonic transducer 2, 3 is within the designed for voltage range of the switches 9, 11 (the predetermined range $V_H$, $V_L$), so that an induced ringing voltage 23 is not coupled to the received signal 10 side. FIG. 15 presents a measurement of the received signal 10 when self-oscillation 22 of the transmitting ultrasonic transducer 2, 3 induces a ringing voltage 23 which exceeds the designed for voltage range of the switches 9, 11 (the predetermined range $V_H$, $V_L$).

Each of FIGS. 14 and 15 shows a portion of the conditioned signal 13 after digitisation by the controller 7. The vertical axes in FIGS. 14 and 15 represent signal amplitude in analog-to-digital converter (ADC) counts, and are proportional to the voltage of the conditioned signal 13. The horizontal axes represent time in microseconds, μs. The received signal 10 from gas (in this case air) which is used for time-of-flight measurements starts at around 150 μs. Before $t_1 \approx 50$ μs, the observed oscillation in FIGS. 14 and 15 is due to capacitive coupling of the drive signal 8 into the electronics which process the received signal 10. At $t_1 \approx 50$ μs, the drive signal 8 stops, and the output of the controller 7 providing the drive signal is set to $V_{RC}=V_{CC}$. As explained hereinbefore, the transmitting ultrasonic transducer 2, 3 continues to self-oscillate 22, and if the induced ringing voltage 23 exceeds the predetermined range $V_H$, $V_L$ of electronics connected between the transmitting ultrasonic transducer 2, 3 and the electronics which process the received signal 10, then a leakage current $I_B$ may be coupled into the path of the received signal 10.

As may be observed from FIG. 15, when interference occurs, this may cause a significant spike 28 which then decays as the self-oscillation 22 decays. If the actual received signal 10 arrives before any interference has fully decayed, then this may cause errors in the time-of-flight measurements. One option would be to simply increase the length d of the flow tube 4 to ensure that there is time for any interference to die down. However, this will prevent a flow rate meter 1 from being compact.

The methods of the present specification address the problem in a different way, by reducing or preventing such interference by maintaining the voltage $V_T(t)$ across a transmitting ultrasonic transducer 2, 3 within the predetermined range $V_H$, $V_L$. Using the methods of the present specification, the length d separating the first and second ultrasonic transducers 2, 3 may be relatively shorter, whilst retaining a simple design of ultrasonic time-of-flight flow rate meter.

Figure 16:
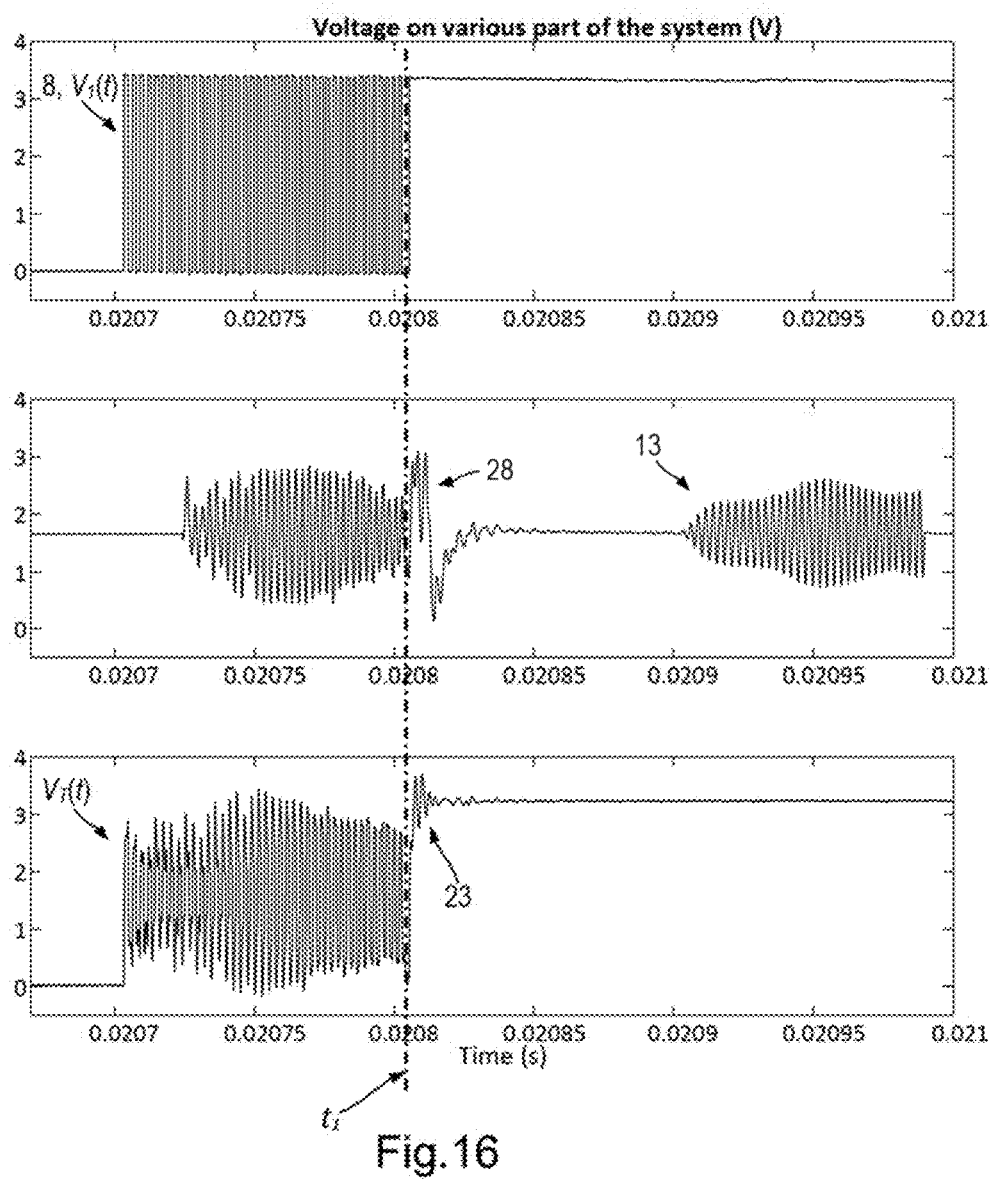
FIG. 16 presents a comparison of a driving signal which includes only a first waveform with the corresponding a received signal and the voltage across a driven ultrasonic transducer.

Referring also to FIG. 16, further measurements relating to the measurements of FIG. 15 are plotted.

The top panel of FIG. 16 shows a measured drive signal 8 which includes only a first waveform $V_1(t)$. In the example measured, the drive signal 8 was clamped to the supply voltage $V_{RU}=V_{CC}=3.3$ V when the first waveform $V_1(t)$ finished at time $t_1$. The middle panel of FIG. 16 shows the conditioned signal 13 shown in FIG. 15 across a longer period of time. The bottom panel of FIG. 16 shows the voltage $V_T(t)$ across the transmitting ultrasonic transducer 2, 3. It may be observed that an induced ringing voltage 23 occurs which significantly exceeds the supply voltage $V_{RU}=V_{CC}=3.3$ V. This induced ringing voltage 23 is the cause of the voltage spike 28 observed in the corresponding conditioned signal 13 (middle panel).

To obtain the data plotted in FIG. 16, the transmitting ultrasonic transducer 2, 3 was driven using a first waveform $V_1(t)$ in the form of a linear chirp having an end frequency of $f(t_1)=437$ kHz.

Figure 17:
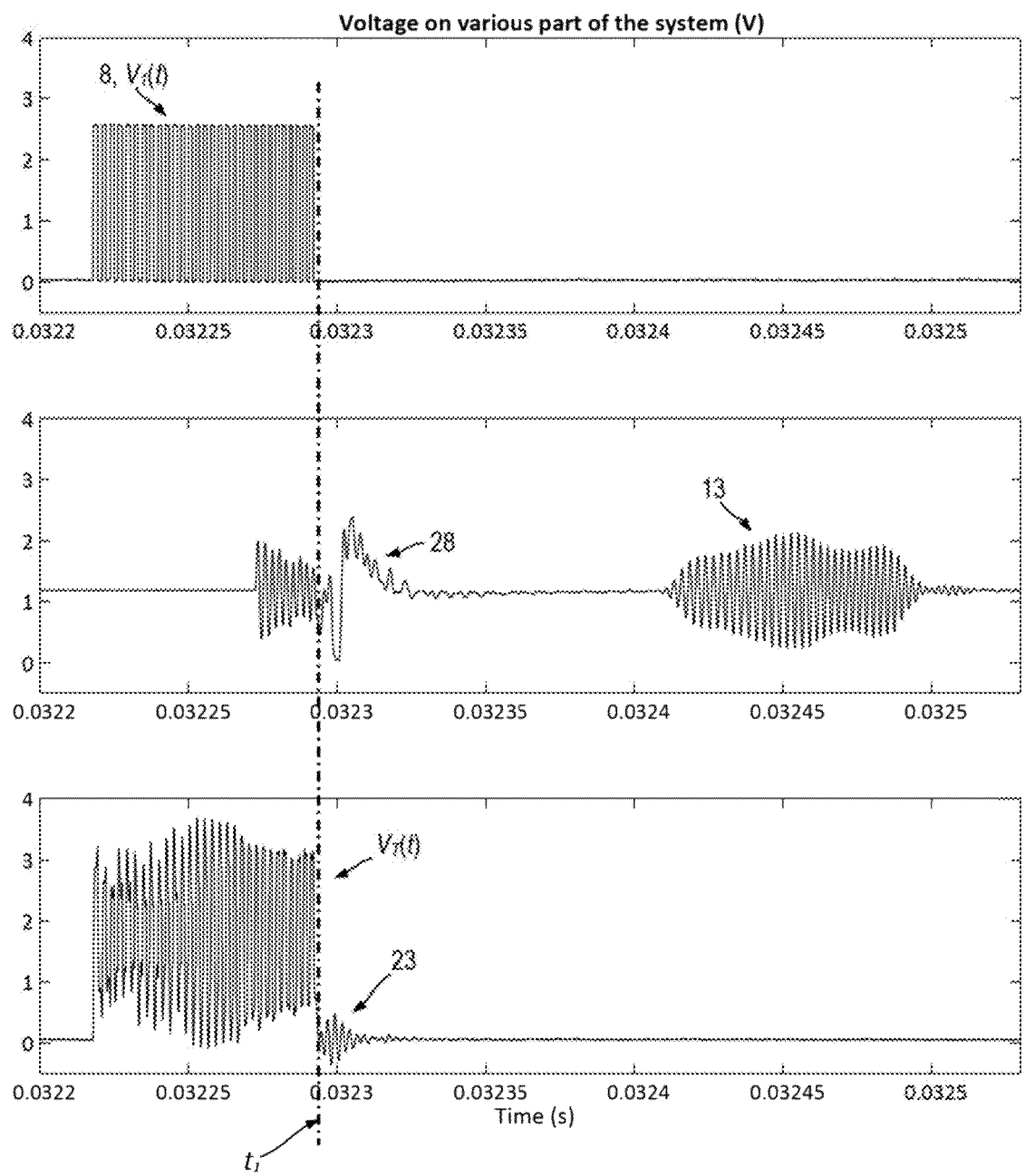
FIG. 17 presents a further comparison of a driving signal which includes only a first waveform with the corresponding received signal and the voltage across a driven ultrasonic transducer.

Referring also to FIG. 17, the driving signal 8, received signal 10 and voltage $V_T(t)$ across the transmitting ultrasonic transducer 2, 3 are shown for an experiment which was the same as for FIG. 16, except that the drive signal 8 was clamped to the ground voltage $V_{RL}=GND=0$ V when the first waveform $V_1(t)$ finished at time $t_1$.

Similar to FIG. 16, in FIG. 17 an induced ringing voltage 23 which dips significantly below the GND voltage of 0 V may be observed, leading to interference in the form of a spike 28 in the corresponding conditioned signal 13.

Experimental Verification of the Method

Figure 18:
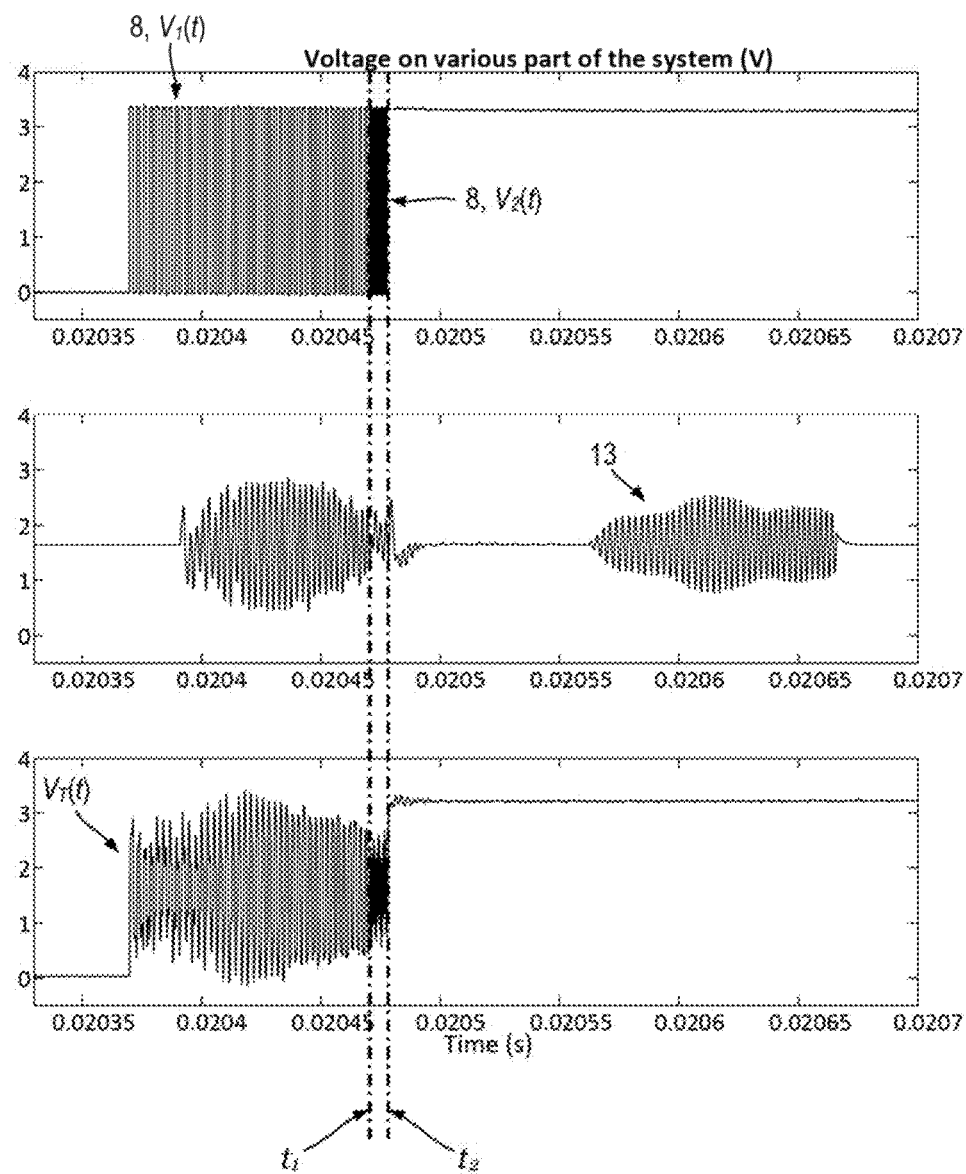
FIG. 18 presents a comparison of a driving signal which includes first and second waveforms with the corresponding received signal and the voltage across a driven ultrasonic transducer.

Referring also to FIG. 18, experimental measurements are presented which correspond to an application of the first method of the present specification.

The top panel of FIG. 18 shows a measured drive signal 8 which includes a first waveform $V_1(t)$ followed by a second waveform $V_2(t)$ having a significantly higher base frequency $f_{B2}$. In the example measured, the drive signal 8 was clamped to the supply voltage $V_{RU}=V_{CC}=3.3$ V when the second waveform $V_2(t)$ finished at time $t_2$. The middle panel of FIG. 18 shows the conditioned signal 13. The bottom panel of FIG. 18 shows the voltage $V_T(t)$ across the transmitting ultrasonic transducer 2, 3.

Figure 19:
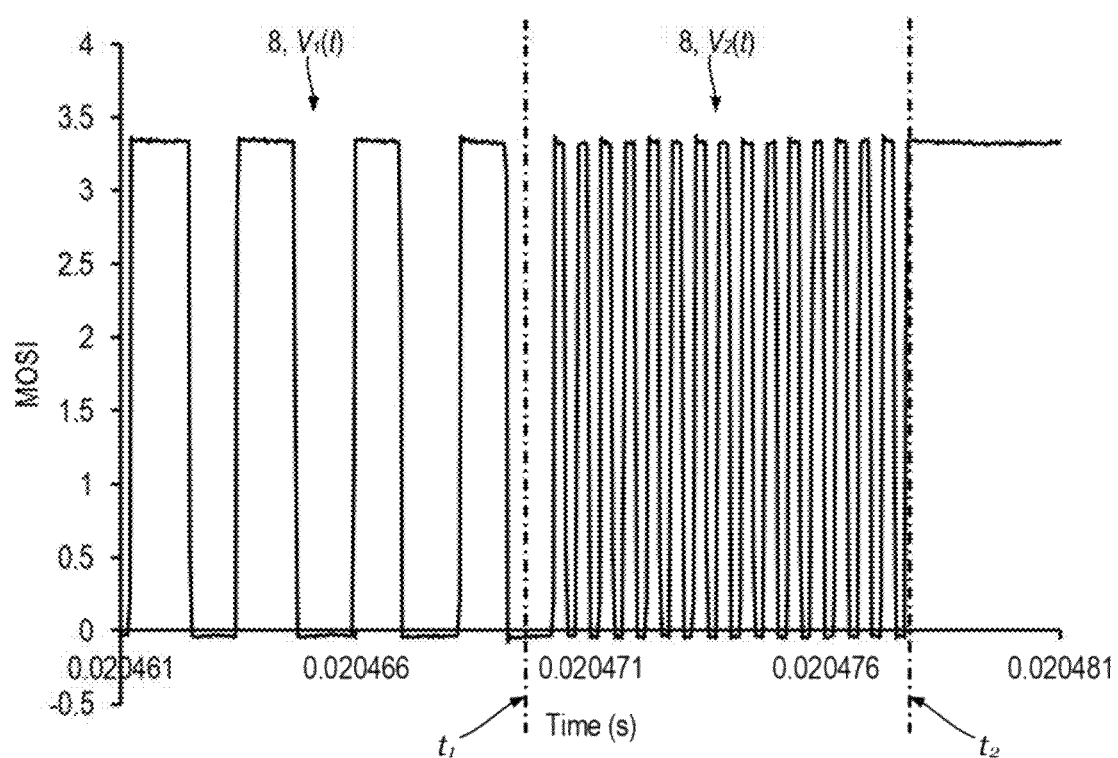
FIG. 19 presents a portion of the driving signal presented in FIG. 18 on a shorter timebase.

Referring also to FIG. 19, the data shown in the top subplot of FIG. 18 is shown on a shorter timebase focused around the second duration $\Delta t_2$.

Figure 20:
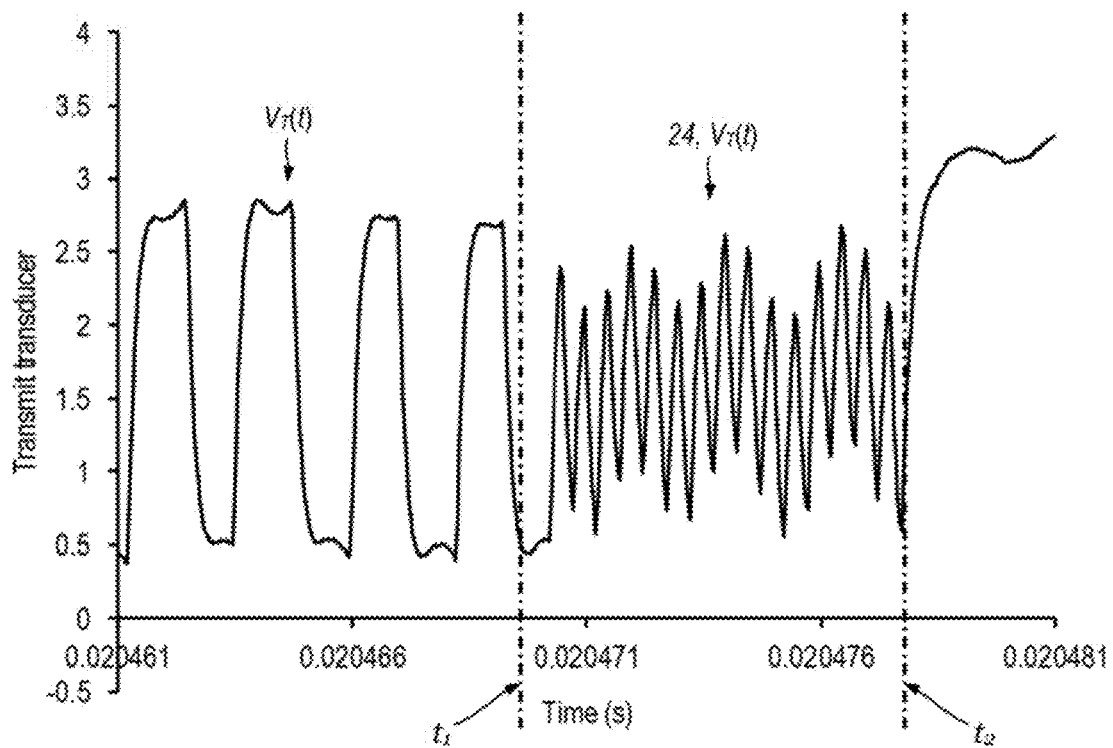
FIG. 20 presents a portion of the voltage across a driven ultrasonic transducer presented in FIG. 18 on a shorter timebase.

Referring also to FIG. 20, the data shown in the bottom subplot of FIG. 18 is shown on the same timebase as FIG. 19.

It may be observed that the modified ringing voltage 24 observed during the second duration $\Delta t_2$ remains bounded between $V_{RL}=GND=0$ and $V_{RU}=V_{CC}=3.3$ V. Although a small amount of ringing is still observed at the end of the second waveform $V_2(t)$, the amplitude is greatly reduced as the self-oscillation 22 has had time to decay.

Modifications

It will be appreciated that many modifications may be made to the embodiments hereinbefore described. Such modifications may involve equivalent and other features which are already known in the design and use of ultrasonic time-of-flight flow meters, and which may be used instead of, or in addition to, features already described herein. Features of one embodiment may be replaced or supplemented by features of another embodiment.

Figure 21:
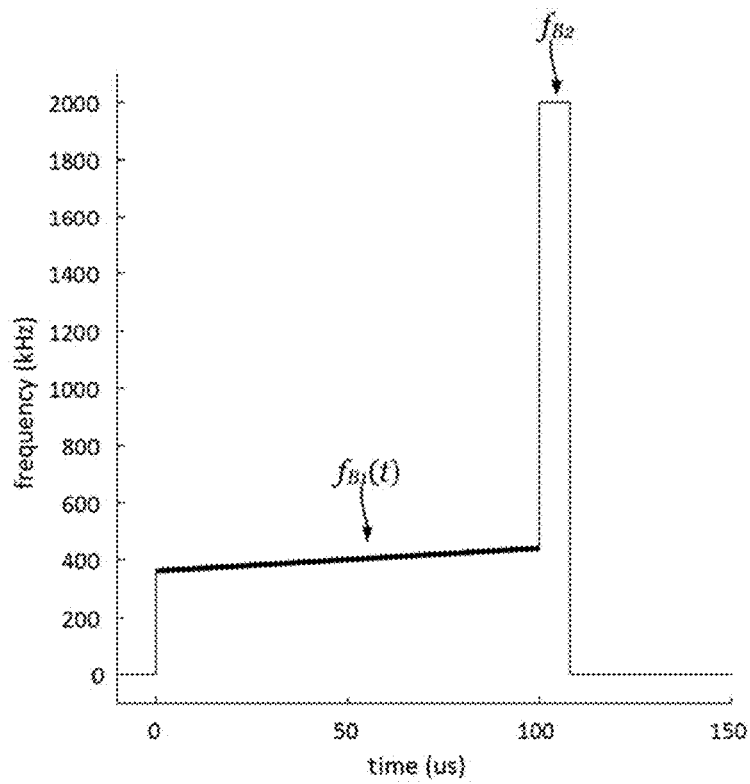
FIG. 21 illustrates an example of a frequency variation of first and second waveforms.

Referring also to FIG. 21, an example according to the method is illustrated.

The first waveform $V_1(t)$ may have a base frequency $f_{B1}(t)$ which varies with time to provide a linear chirp spanning the bandwidth $\delta f_1$ of a primary resonance $f_1$. The second waveform $V_2(t)$ has a fixed base frequency $f_{B2}$ which is significantly higher than the final base frequency $f_{B1}(t_1)$ of the first waveform $V_1(t)$, and outside the bandwidth $\delta f_1$ of a primary resonance $f_1$, or indeed any other resonance $f_2$, $f_3$ and so forth.

Figure 22:
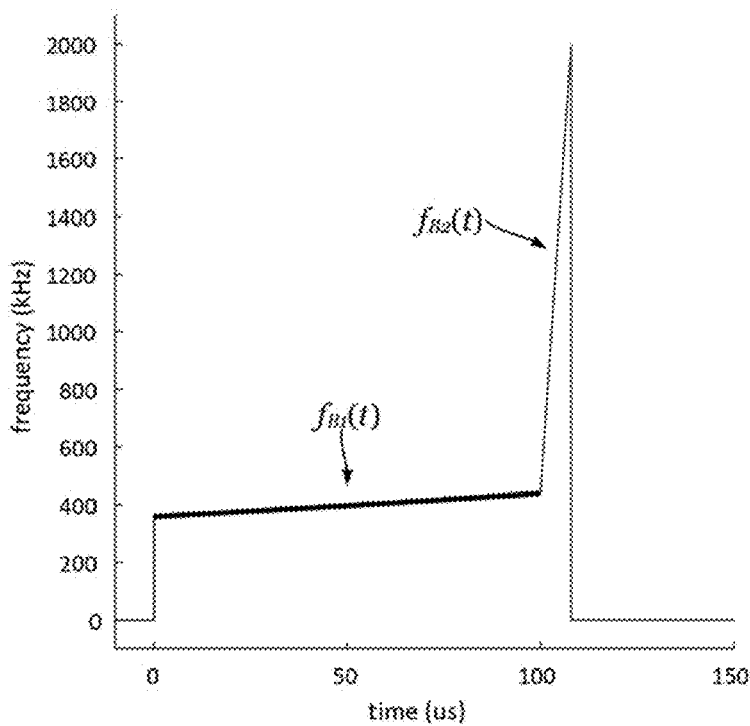
FIG. 22 illustrates a further example of a frequency variation of first and second waveforms.

Referring also to FIG. 22, an example according to the method is illustrated.

The first waveform $V_1(t)$ may have a base frequency $f_{B1}(t)$ which varies with time to provide an exponential chirp spanning the bandwidth $\delta f_1$ of a primary resonance $f_1$. The second waveform $V_2(t)$ may have a base frequency $f_{B2}(t)$ which varies with time to provide a linear or exponential chirp, which moves outside of the bandwidth $\delta f_1$ of the primary resonance $f_1$ with a greatly increased gradient. For example, the base frequencies $f_{B1}, f_{B2}$ may satisfy:

$$f_{B1}(t_1) = f_{B2}(t_1) \qquad (8)$$

$$\left. \frac{df_{B1}}{dt} \right|_{t_1} \ll \left. \frac{df_{B2}}{dt} \right|_{t_1}$$

Figure 23:
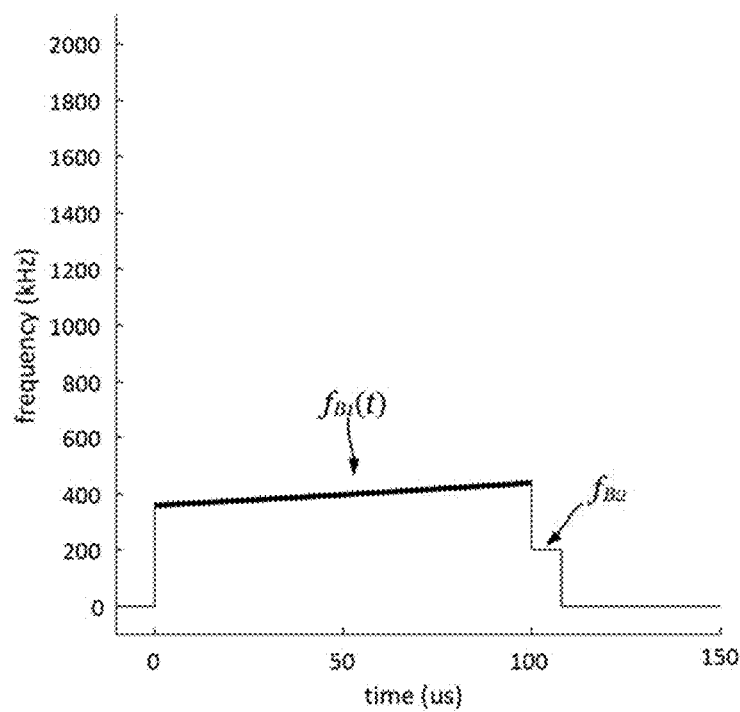
FIG. 23 illustrates a further example of a frequency variation of first and second waveforms.

Referring also to FIG. 23, an example according to the method is illustrated.

The first waveform $V_1(t)$ may have a base frequency $f_{B1}(t)$ which varies with time to provide an exponential chirp spanning the bandwidth $\delta f_1$ of a primary resonance $f_1$. The second waveform $V_2(t)$ has a fixed base frequency $f_{B2}$ which is significantly lower than the final base frequency $f_{B1}(t_1)$ of the first waveform $V_1(t)$, and outside the bandwidth $\delta f_1$ of a primary resonance $f_1$, or indeed any other resonance $f_2$, $f_3$ and so forth.

Although specific examples of the first and second waveforms $V_1(t)$, $V_2(t)$ have been described and illustrated, the methods of the present specification are not limited thereto. Any combination of first and second waveforms $V_1(t)$, $V_2(t)$ may be used, provided that there is a discontinuity between the first waveform $V_1(t)$, and that the second waveform $V_2(t)$, and the second duration $\Delta t_2$ are configured to maintain a voltage $V_T(t)$ across the ultrasonic transducer 2, 3 within the predetermined range $V_H$, $V_L$.

For example, the first waveform $V_1(t)$ may have a substantially constant base frequency $f_{B1}$. Equally, the second waveform $V_2(t)$ may have a substantially constant base frequency $f_{B2}$. Depending upon the application, the term "substantially" may correspond to a tolerance of ±5%, or ±10%. The base frequency $f_{B1}(t)$ of the first waveform $V_1(t)$ may vary as a function of time, for example according to a linear, exponential or reciprocal chirp. The base frequency $f_{B2}(t)$ of the second waveform $V_2(t)$ may vary as a function of time, for example according to a linear, exponential or reciprocal chirp. The frequency variation of the second waveform $V_2(t)$ with time may be a continuous extension of the frequency variation of the first waveform $V_1(t)$ with time, and the discontinuity may occur in other properties such as phase, duty cycle, and so forth.

The methods of the present specification may be applied to measure flow rates of any fluids, including liquids or gasses. The methods may be used to measure the flow rate of natural gas. The methods may be used to measure the flow rate of water. The methods may be used to measure a flow rate of a fluid, and the measured flow rate may be used for fiscal metering purposes.

Although the ultrasonic time-of-flight flow rate meter 1 has been described with reference to ultrasonic transducers, for example piezoelectric transducers, which are connected between ground and a driving potential, this need not be the case. In some implementations of the methods of the present specification, the ultrasonic transducers 2, 3 may be driven using a differential driving circuit. For example, instead of connecting one end of an ultrasonic transducer 2, 3 to ground and the other to drive signal 8 or upper/lower rail voltage, an ultrasonic transducer 2, 3 used to transmit may be connected across the outputs of a differential drive circuit. Similarly, an ultrasonic transducer 2, 3 used to receive a signal may be connected across the inputs of a differential amplifier.

An ultrasonic time-of-flight flow meter 1 according to the present specification may be a gas meter for measuring flow rates of natural gas. The first waveform $V_1(t)$ may comprise a linear chirp composed of square wave or top-hat pulses. The linear chirp may span a range of frequencies between and including 360 kHZ and 440 kHz, i.e. $f_{B1}(t_0)$=360 kHz and $f_{B1}(t_1)$=440 kHz. A bandwidth $\delta f_1$ of a primary resonance $f_1$ of the ultrasonic transducer may be within the range of frequencies between and including 360 kHZ and 440 kHz. Each individual pulse making up the first waveform $V_1(t)$ may have a duration of approximately 2.5 microseconds. The first duration $\Delta t_1$ may be approximately 100 μs. The first duration $\Delta t_1$ may encompass about 40 individual pulses. The second waveform $V_2(t)$ may comprise a pulsed waveform having a base frequency $f_{B2}$=2 MHz. The base frequency $f_{B2}$=2 MHz may be outside any bandwidth $\delta f_1$, $\delta f_2$, $\delta f_3$ which corresponds to a resonance of the ultrasonic transducer 2, 3. The second duration $\Delta t_2$ may be approximately 8 μs. The second duration $\Delta t_2$ may be between 2 to 5 times a duration of an average period of the first waveform $V_1(t)$. The distance d separating the ultrasonic transducers 2, 3 may be between and including 50 mm and 100 mm. The distance d separating the ultrasonic transducers 2, 3 may be approximately 70 mm.

An ultrasonic time-of-flight flow meter 1 according to the present specification may be a water meter for measuring flow rates of water. The first waveform $V_1(t)$ may comprise a pulsed waveform having a substantially constant base frequency $f_{B1}$. The base frequency $f_{B1}$ of the first waveform $V_1(t)$ may be between and including the range of 0.8 MHz to 1.2 MHz. The base frequency $f_{B1}$ of the first waveform $V_1(t)$ may be approximately 1 MHz. The base frequency $f_{B1}$ of the first waveform $V_1(t)$ may be tuned to a primary resonance frequency $f_1$ of the ultrasonic transducer 2, 3. The first duration $\Delta t_1$ may be approximately 17 microseconds. The first duration $\Delta t_1$ may encompass about 17 cycles of the first waveform $V_1(t)$. The second waveform $V_2(t)$ may comprise a pulsed waveform having a base frequency $f_{B2}$ of 5 MHz. The base frequency $f_{B2}$ of 5 MHz may be outside any bandwidth $\delta f_1$, $\delta f_2$, $\delta f_3$ which corresponds to a resonance of the ultrasonic transducer 2, 3. The second duration $\Delta t_2$ may be approximately 2 microseconds. The distance d separating the ultrasonic transducers 2, 3 may be between and including 90 mm and 135 mm. The distance d separating the ultrasonic transducers 2, 3 may be approximately 115 mm.

Methods have been described in which an ultrasonic transducer 2, 3 is driven using a first waveform $V_1(t)$ for a first duration $\Delta t_1$, followed by driving using a second waveform $V_2(t)$ for a second duration $\Delta t_2$. However, in other examples, the drive signal 6 may include a third waveform $V_3(t)$, a fourth waveform $V_4(t)$, and so forth. For example, immediately following the first waveform $V_1(t)$, the drive signal 6 may include a second waveform $V_2(t)$ in the form of a linear or exponential chirp which rapidly shifts to a frequency outside any bandwidth $\delta f_1$, $\delta f_2$, $\delta f_3$ which corresponds to a respective resonance of the ultrasonic transducer 2, 3. The third waveform $V_3(t)$ may be selected from a third group consisting of a third fixed frequency waveform, a third exponential chirp, a third linear chirp or a third reciprocal chirp. The third waveform $V_3(t)$ may be continuous or discontinuous with the second waveform $V_2(t)$.

Similarly a fourth waveform $V_4(t)$ and/or further waveforms may be inserted into the oscillation exciting segment, $t_0$ to $t_1$, of the drive signal, or into the non-exciting segments $t_1$ to $t_2$. Such fourth $V_4(t)$ and/or further waveforms may be selected from corresponding groups consisting of fixed frequency waveforms, exponential chirps, linear chirps or reciprocal chirps.

In a further example, the first waveform $V_1(t)$ may include two or more distinct sub-waveforms $V_{1A}(t)$, $V_{1B}(t)$ and so forth. Each sub-waveform $V_{1A}(t)$, $V_{1B}(t)$ of the first waveform $V_1(t)$ may be configured to cause oscillation of the ultrasonic transducer 2, 3. The two or more sub-waveforms $V_{1A}(t)$, $V_{1B}(t)$ may be continuous or discontinuous with preceding or following sub-waveforms $V_{1A}(t)$, $V_{1B}(t)$. When the first waveform $V_1(t)$ includes two or more sub-waveforms $V_{1A}(t)$, $V_{1B}(t)$ and so forth, there is a discontinuity between the final sub-waveform of the first waveform $V_1(t)$ and the second waveform $V_2(t)$.

Similarly, the second waveform $V_2(t)$ may include two or more distinct sub-waveforms $V_{2A}(t)$, $V_{2B}(t)$ and so forth. Each sub-waveform $V_{2A}(t)$, $V_{2B}(t)$ of the second waveform $V_2(t)$ may be configured, in combination with the overall second duration $\Delta t_2$, to maintain the voltage across the ultrasonic transducer $V_T(t)$ within the predetermined range $V_H$, $V_L$. The two or more sub-waveforms $V_{2A}(t)$, $V_{2B}(t)$ may be continuous or discontinuous with preceding or following sub-waveforms $V_{2A}(t)$, $V_{2B}(t)$. When the second waveform $V_2(t)$ includes two or more sub-waveforms $V_{2A}(t)$, $V_{2B}(t)$ and so forth, there is a discontinuity between the first waveform $V_1(t)$ and the first sub-waveform $V_{2A}(t)$ of the second waveform $V_2(t)$.

In one example of a drive signal 8 including sub-waveforms, a first waveform $V_1(t)$ may excite the transmitting ultrasonic transducer 2, 3. A second waveform $V_2(t)$ may include first and second sub-waveforms $V_{2A}(t)$, $V_{2B}(t)$. The first sub-waveform $V_{2A}(t)$ of the second waveform $V_2(t)$ may be the same as the first waveform $V_1(t)$, except for a phase shift of between π/2 to 3π/2, so that the first sub-waveform $V_{2A}(t)$ of the second waveform $V_2(t)$ may dampen or substantially dampen the self-oscillation 22 of a transmitting ultrasonic transducer 2, 3. Finally, the second sub-waveform $V_{2B}(t)$ of the second waveform $V_2(t)$ may have a base frequency $f_B$ which is outside any bandwidth $\delta f_1$, $\delta f_2$, $\delta f_3$ that corresponds to a respective resonance of the ultrasonic transducer 2, 3. The first sub-waveform $V_{2A}(t)$ of the second waveform $V_2(t)$ may dampen the self-oscillation 22, whilst the second sub-waveform $V_{2B}(t)$ of the second waveform $V_2(t)$ maintains the induced voltage 24 resulting from any residual self-oscillation safely within the predetermined range $V_H$, $V_L$. In this way, the total length of self-oscillation 22 may be reduced, and the distance d separating a pair of ultrasonic transducers 2, 3 may be further reduced.

An ultrasonic time-of-flight flow rate meter 1 has been described in which a single pair of first and second ultrasonic transducers 2, 3 is used for time-of-flight measurements. However, in other examples, more than one pair of ultrasonic transducers 2, 3 may be used. In such examples, any ultrasonic transducer 2, 3 which is used to generate an ultrasound pulse may be driven using a drive signal 8 comprising first and second waveforms $V_1(t)$, $V_2(t)$ as described (each optionally including two or more sub-waveforms $V_{1A}(t)$, $V_{1B}(t)$, $V_{2A}(t)$, $V_{2B}(t)$).

Although claims have been formulated in this application to particular combinations of features, it should be understood that the scope of the disclosure of the present invention also includes any novel features or any novel combination of features disclosed herein either explicitly or implicitly or any generalization thereof, whether or not it relates to the same invention as presently claimed in any claim and whether or not it mitigates any or all of the same technical problems as does the present invention. The applicant hereby gives notice that new claims may be formulated to such features and/or combinations of such features during the prosecution of the present application or of any further application derived therefrom.

The invention claimed is:

1. A method for an ultrasonic time-of-flight flow meter, comprising:
    driving an ultrasonic transducer using a first waveform for a first duration, the first waveform configured to cause oscillation of the ultrasonic transducer;
    driving the ultrasonic transducer using a second waveform for a second duration,
wherein the second waveform does not excite further oscillation of the ultrasonic transducer,
    wherein there is a discontinuity between the first waveform and the second waveform, and wherein the second waveform and the second duration are configured to maintain a voltage across the ultrasonic transducer within a predetermined range.

2. A method according to claim 1, wherein the second duration is configured to be sufficiently long to allow an oscillation energy of the transducer to reduce to a level whereby the voltage across the ultrasonic transducer will remain within the predetermined range after the end of the second duration.

3. A method according to claim 1, wherein the predetermined range is a designed for driving voltage range of the ultrasonic transducer, or the designed for driving voltage range of the ultrasonic transducer plus an overvoltage tolerance.

4. A method according to claim 1, wherein the predetermined range is a rail-to-rail voltage of a further component which is connected to the ultrasonic transducer, or the rail-to-rail voltage of the further component plus an overvoltage tolerance.

5. A method according to claim 1, wherein the first waveform has a frequency spectrum in which a majority of the power is within one or more bandwidths corresponding to respective resonances of the ultrasonic transducer; and
    wherein the second waveform has a frequency spectrum in which a majority of the power is outside the one or more bandwidths corresponding to respective resonances of the ultrasonic transducer.

6. A method according to claim 1, wherein the first waveform has a substantially constant base frequency.

7. A method according to claim 1, wherein the second waveform has a substantially constant base frequency.

8. A method according to claim 1, wherein the frequency of the first waveform varies as a function of time.

9. A method according to claim 1, wherein the frequency of the second waveform varies as a function of time.

10. A method according to claim 1, wherein the method is used to measure the flow rate of a liquid.

11. A method according to claim 1, wherein the method is used to measure the flow rate of a gas.

12. A method according to claim 1, wherein the method is used to measure the flow rate of water.

13. A method according to claim 1, wherein the method is used to measure the flow rate of natural gas.

14. A method according to claim 1, wherein the method is used to measure a flow rate used for fiscal metering purposes.

15. An ultrasonic time-of-flight flow meter comprising:
    a first ultrasonic transducer and a second ultrasonic transducer spaced apart along a fluid flow path and configured such that a transmission path between the first and second ultrasonic transducers has a component in a direction parallel to the fluid flow path;
    a controller configured to drive the first and second ultrasonic transducers alternately, wherein the controller is configured to:
        drive the driven ultrasonic transducer using a first waveform for a first duration, the first waveform configured to cause oscillation of the driven ultrasonic transducer;
        drive the driven ultrasonic transducer using a second waveform for a second duration, wherein the second waveform is configured not to excite further oscillation of the ultrasonic transducer;
        wherein there is a discontinuity between the first waveform and the second waveform, and wherein the second waveform and the second duration are configured to maintain a voltage across the driven ultrasonic transducer within a predetermined range.

16. An ultrasonic time-of-flight flow meter according to claim 15, wherein the second duration is configured to be sufficiently long to allow an oscillation energy of the driven ultrasonic transducer to reduce to a level whereby the voltage across the driven ultrasonic transducer will remain within the predetermined range after the end of the second duration.

17. An ultrasonic time-of-flight flow meter according to claim 15, wherein the first waveform has a frequency spectrum in which a majority of the power is within one or more bandwidths corresponding to respective resonances of the driven ultrasonic transducer; and
    wherein the second waveform has a frequency spectrum in which a majority of the power is outside the one or more bandwidths corresponding to respective resonances of the driven ultrasonic transducer.

18. An ultrasonic time-of-flight flow meter according to claim 15, wherein the second waveform is configured to suppress coupling between the first and second ultrasonic transducers.

* * * * *